(12) United States Patent
Chien et al.

(10) Patent No.: US 10,267,803 B2
(45) Date of Patent: Apr. 23, 2019

(54) HCV NS4A/MODIFIED NS3 POLYPEPTIDES AND USES THEREOF

(71) Applicants: ORTHO-CLINICAL DIAGNOSTICS, INC., Raritan, NJ (US); ORTHO CLINICAL DIAGNOSTICS, K.K., Tokyo (JP); GRIFOLS WORLDWIDE OPERATIONS LIMITED, Dublin (IE)

(72) Inventors: David Y. Chien, Alamo, CA (US); Doris Guenzi Coit, Petaluma, CA (US); Toshiya Fujihara, Urayasu (JP); Alexander Gyenes, San Francisco, CA (US); John Andrew Hall, Rohnert Park, CA (US); Angelica Medina-Selby, San Francisco, CA (US); Jian Zheng, Raritan, NJ (US)

(73) Assignee: ORTHO-CLINICAL DIAGNOSTICS, INC., Raritan, NJ (US)

( * ) Notice: Subject to any disclaimer, the term of this patent is extended or adjusted under 35 U.S.C. 154(b) by 0 days.

(21) Appl. No.: 15/025,301

(22) PCT Filed: Jun. 22, 2015

(86) PCT No.: PCT/US2015/036941
§ 371 (c)(1),
(2) Date: Mar. 28, 2016

(87) PCT Pub. No.: WO2016/160046
PCT Pub. Date: Oct. 6, 2016

(65) Prior Publication Data
US 2018/0011096 A1     Jan. 11, 2018

Related U.S. Application Data

(60) Provisional application No. 62/139,183, filed on Mar. 27, 2015.

(51) Int. Cl.
*C07K 14/005* (2006.01)
*C12Q 1/70* (2006.01)
*G01N 33/576* (2006.01)

(52) U.S. Cl.
CPC ....... *G01N 33/5767* (2013.01); *C07K 14/005* (2013.01); *C07K 2319/00* (2013.01); *C12N 2770/24222* (2013.01); *C12Q 1/70* (2013.01); *G01N 2333/186* (2013.01); *G01N 2469/20* (2013.01)

(58) Field of Classification Search
None
See application file for complete search history.

(56) References Cited

U.S. PATENT DOCUMENTS

| | | | |
|---|---|---|---|
| 5,871,904 A | 2/1999 | Kashiwakuma et al. | |
| 6,150,087 A | 11/2000 | Chien | |
| 6,211,338 B1 | 4/2001 | Malcolm et al. | |
| 6,630,298 B2 | 10/2003 | Chien et al. | |
| 6,632,601 B2 | 10/2003 | Chien et al. | |
| 7,491,808 B2 | 2/2009 | Chien et al. | |

FOREIGN PATENT DOCUMENTS

| | | | |
|---|---|---|---|
| EP | 0 318 216 A1 | | 5/1989 |
| EP | 0 388 232 A1 | | 9/1990 |
| WO | WO 89/04669 A1 | | 6/1989 |
| WO | WO 90/11089 A1 | | 10/1990 |
| WO | WO 90/14435 A1 | | 11/1990 |
| WO | WO 93/00365 A2 | | 1/1993 |
| WO | WO 94/01778 A1 | | 1/1994 |
| WO | WO 97/44469 A2 | | 11/1997 |
| WO | WO 2006/024020 | * | 3/2006 |
| WO | WO 2006/024020 A2 | | 3/2006 |

OTHER PUBLICATIONS

GenBank Accession No. AJ238800.1 (5 pages) (Apr. 15, 2005).
GenBank Accession No. AJ238799.1 (5 pages) (Apr. 15, 2005).
Chien D.Y. et al., "Diagnosis of Hepatitis C Virus (HCV) Infection Using an Immunodominant Chimeric Polyprotein to Capture Circulating Antibodies: Reevaluation of the Role of HCV in Liver Disease", Proc. Natl. Acad. Sci. USA 89:10011-10015 (Nov. 1992).
Chien D.Y. et al., "Use of Recombinant HCV Antigen in the Serodiagnosis of Hepatitis C Virus Infection: Significant Improvement in HCV Antibody Detection as Compared With the First Generation HCV C100-3 ELISA and the Synthetic Peptide EIA Tests", Journal of Gastroenterology and Hepatology 8:S33-S39 (1993).
Choo Q-L et al., "Genetic Organization and Diversity of the Hapatitis C Virus", Proc. Natl. Acad. Sci. USA 88:2451-2455 (Mar. 1991).
Choo Q-L et al., "Hepatitis C Virus: The Major Causative Agent of Viral Non-A, Non-B Hepatitis", British Medical Bulletin 46(2):423-441 (1990).
Choo Q-L et al., "Isolation of a cDNA Clone Derived from a Blood-Borne Non-A, Non-B Viral Hepatitis Genome", Science 244:359-362 (Apr. 21, 1989).
Ebeling F. et al., "Recombinant Immunoblot Assay for Hepatitis C Virus Antibody as Predictor of Infectivity", The Lancet 335:982-983 (Apr. 21, 1990).
Han J.H. et al., "Characterization of the Terminal Regions of Hepatitis C Viral RNA: Identification of Conserved Sequences in the 5' Untranslated Region and Poly(A) Tails at the 3' End", Proc. Natl. Acad. Sci. USA 88:1711-1715 (Mar. 1991).
Houghton M. et al., "Molecular Biology of the Hepatitis C Viruses: Implications for Diagnosis, Development and Control of Viral Diseases", Hepatology 14(2):381-388 (1991).
Kuo G. et al., "An Assay for Circulating Antibodies to a Major Etiologic Virus of Human Non-A, Non-B Hepatitis", Science 244:362-364 (Apr. 1989).

(Continued)

*Primary Examiner* — Nicole Kinsey White
(74) *Attorney, Agent, or Firm* — K&L Gates LLP; Louis C. Cullman; Michelle Glasky Bergman

(57) ABSTRACT

Modified hepatitis C virus polypeptides are described. The polypeptides include the HCV NS4a domain and modified NS3 domain. The polypeptides retain conformational epitopes. HCV immunoassays including the polypeptides are also described.

17 Claims, 6 Drawing Sheets
Specification includes a Sequence Listing.

(56) References Cited

OTHER PUBLICATIONS

Lin S. et al., "Design of Novel Conformational and Genotype-Specific Antigens for Improving Sensitivity of Immunoassays for Hepatitis C Virus-Specific Antibodies", Journal of Clinical Microbiology 43(8):3917-3924 (Aug. 2005).
Rimmert B. et al., "A 3D Structural Model and Dynamics of Hepatitis C Virus NS3/4A Protease (Genotype 4a, Strain ED43) Suggest Conformational Instability of the Catalytic Triad: Implications in Catalysis and Drug Resistivity", Journal of Biomolecular Structure and Dynamics 32(6):950-958 (2014).
Simmonds P. et al., "Classification of Hepatitis C Virus into Six Major Genotypes and a Series of Subtypes by Phylogenetic Analysis of the NS-5 Region", Journal of General Virology 74:2391-2399 (1993).
Vajdy M. et al., "Hepatitis C Virus Polyprotein Vaccine Formulations Capable of Inducing Broad Antibody and Cellular Immune Responses", Journal of General Virology 87:2253-2262 (2006).
Van Der Poel C.L. et al., "Confirmation of Hepatitis C Virus Infection by New Four-Antigen Recombinant Immunoblot Assay", The Lancet 337:317-319 (Feb. 9, 1991).
Van Der Poel C.L. et al., "Infectivity of Blood Seropositive for Hepatitis C Virus Antibodies", The Lancet 335:558-560 (Mar. 10, 1990).
International Search Report and Written Opinion dated Dec. 8, 2015 received from International Application No. PCT/US15/36941.

\* cited by examiner

FIG. 1

| C 1-191 | E1 192-383 | E2 384-746 | P7 | NS2 810-1026 | NS3 1027-1657 | NS4a | NS4b 1712-1972 | NS5a 1973-2420 | NS5b 2421-3011 |

HCV1

*with reference to SEQ ID NO:1

*with reference to SEQ ID NO:1

HCV NS4A/MODIFIED NS3 POLYPEPTIDES AND USES THEREOF

CROSS-REFERENCE TO RELATED APPLICATIONS

This application is the § 371 national phase of International Application No. PCT/US2015/036941 filed Jun. 22, 2015, which claims the benefit of U.S. Provisional Application No. 62/139,183, filed Mar. 27, 2015.

STATEMENT REGARDING FEDERALLY SPONSORED RESEARCH OR DEVELOPMENT

Not applicable.

INCORPORATION BY REFERENCE OF SEQUENCE LISTING

The Sequence Listing in an ASCII text file, named as 32955_Sequence_Listing.txt of 29 KB, created on Mar. 25, 2016, and submitted to the United States Patent and Trademark Office via EFS-Web, is incorporated herein by reference.

FIELD OF THE INVENTION

The invention relates generally to hepatitis C virus (HCV) constructs and methods of using the same. More particularly, the invention relates to immunogenic, immunoreactive HCV polypeptides with NS4a and modified NS3 domains. The modified polypeptides retain conformational epitopes and are therefore useful in immunoassays for diagnosing HCV infection.

BACKGROUND OF THE INVENTION

Hepatitis C Virus (HCV) is the principal cause of parenteral non-A, non-B hepatitis (NANBH) which is transmitted largely through body blood transfusion and body fluid exchange. The virus is present in 0.4 to 2.0% of the general population in the United States. Chronic hepatitis develops in about 50% of infections and of these, approximately 20% of infected individuals develop liver cirrhosis which sometimes leads to hepatocellular carcinoma. Accordingly, the study and control of the disease is of medical importance.

HCV was first identified and characterized as a cause of NANBH by Houghten et al. The viral genomic sequence of HCV is known, as are methods for obtaining the sequence. See, e.g., International Publication Nos. WO 89/04669; WO 90/11089; and WO 90/14436. HCV has a 9.5 kb positive-sense, single-stranded RNA genome and is a member of the Flaviridae family of viruses. At least six distinct, but related genotypes of HCV, based on phylogenetic analyses, have been identified (Simmonds et al., J. Gen. Virol. (1993) 74:2391-2399). The virus encodes a single polyprotein having more than 3000 amino acid residues (Choo et al., Science (1989) 244:359-362; Choo et al., Proc. Natl. Acad. Sci. USA (1991) 88:2451-2455; Han et al., Proc. Natl. Acad. Sci. USA (1991) 88:1711-1715). The polyprotein is processed co- and post-translationally into both structural and non-structural (NS) proteins.

In particular, several proteins are encoded by the HCV genome. The order and nomenclature of the cleavage products of the HCV polyprotein is as follows: NH$_2$—C-E1-E2-P7-NS2-NS3-NS4a-NS4b-NS5a-NS5b-COOH. Initial cleavage of the polyprotein is catalyzed by host proteases which liberate three structural proteins, the N-terminal nucleocapsid protein (termed "core") and two envelope glycoproteins, "E1" (also known as E) and "E2" (also known as E2/NS1), as well as nonstructural (NS) proteins that contain the viral enzymes. The NS regions are termed NS2, NS3, NS4, NS4a, NS4b, NS5a and NS5b. NS2 is an integral membrane protein with proteolytic activity. NS2, either alone or in combination with NS3, cleaves the NS2-NS3 sissle bond which in turn generates the NS3 N-terminus and releases a large polyprotein that includes both serine protease and RNA helicase activities. The NS3 protease serves to process the remaining polyprotein. In particular, the HCV NS3 protein is a 630 amino acid protein containing three functional domains. The serine-like protease domain is located in the amino terminus, whereas helicase and NTPase activity are in the carboxy terminus. The serine protease of NS3 is responsible for the cleavage at the junction of NS3/4a, NS4a/b, NS4b/5a and NS5a/b.

A number of general and specific polypeptides useful as immunological and diagnostic reagents for HCV, derived from the HCV polyprotein, have been described. See, e.g., Houghton et al., European Publication Nos. 318,216 and 388,232; Choo et al., Science (1989) 244:359-362; Kuo et al., Science (1989) 244:362-364; Houghton et al., Hepatology (1991) 14:381-388; Chien et al., Proc. Natl. Acad. Sci. USA (1992) 89:10011-10015; Chien et al., J. Gastroent. Hepatol. (1993) 8:S33-39; Chien et al., International Publication No. WO 93/00365; Chien, D. Y., International Publication No. WO 94/01778. These publications provide an extensive background on HCV generally, as well as on the manufacture and uses of HCV polypeptide immunological reagents. For brevity, therefore, the disclosure of these publications is incorporated herein by reference.

Sensitive, specific methods for screening and identifying carriers of HCV and HCV-contaminated blood or blood products provide an important advance in medicine. Post-transfusion hepatitis (PTH) occurs in approximately 10% of transfused patients, and HCV has accounted for up to 90% of these cases. Patient care as well as the prevention and transmission of HCV by blood and blood products or by close personal contact require reliable diagnostic and prognostic tools. Accordingly, several assays have been developed for the serodiagnosis of HCV infection. See, e.g., Choo et al., Science (1989) 244:359-362; Kuo et al., Science (1989) 244:362-364; Choo et al., Br. Med. Bull. (1990) 46:423-441; Ebeling et al., Lancet (1990) 335:982-983; van der Poel et al., Lancet (1990) 335:558-560; van der Poel et al., Lancet (1991) 337:317-319; Chien, D. Y., International Publication No. WO 94/01778; Valenzuela et al., International Publication No. WO 97/44469; and Kashiwakuma et al., U.S. Pat. No. 5,871,904.

U.S. Pat. No. 6,630,298, incorporated herein by reference in its entirety, describes an HCV antigen/antibody combination assay using an HCV core antibody to detect HCV antigen and NS3/4a epitope to detect HCV antibody. The NS3/4a epitope has NS3 on the amino terminal and NS4a on the carboxy terminal. The protease activity of the NS3 domain is preserved in this epitope, and stability is negatively impacted by the presence of the protease activity.

U.S. Pat. No. 6,632,601, incorporated herein by reference in its entirety, describes immunoassays using NS3/4a conformational epitopes, in combination with multiple epitope fusion antigens (MEFAs). The assays provide methods for detecting early HCV seroconversion. NS3/4a, expressed in yeast and purified under non-denaturing conditions as described in U.S. Pat. No. 6,632,601, contains both protease and helicase function. Because NS3/4a purified in this manner preserves the native conformation, it has been found to be more sensitive than the c200 or c33c antigens in early seroconversion antibody detection. In antibody assays using NS3/4a and MEFA 7.1 as antigens, seroconversion antibodies were detected 2-14 days earlier than then-existing marketed HCV assays. However, the NS3/4a protein undergoes self-hydrolysis and cleaves MEFA 7.1 due to the NS3 protease activity.

U.S. Pat. No. 7,491,808, incorporated herein by reference in its entirety, describes NS3/4a conformational epitopes including mutated NS3 protease domains with reduced proteolytic activity, in combination with MEFAs.

U.S. Pat. No. 6,211,338, incorporated herein by reference in its entirety, describes covalent HCV NS4a/NS3 complexes comprising the central hydrophobic domain of native HCV NS4a peptide, a linker, and the HCV NS3 serine protease domain. The NS4a/NS3 complex is useful for structural determination and determination of mode of binding of HCV inhibitors by NMR spectroscopy.

There continues to remain a need for sensitive, accurate diagnostic and prognostic tools in order to provide adequate patient care as well as to prevent transmission of HCV by blood and blood products or by close personal contact.

BRIEF SUMMARY OF THE INVENTION

The present invention is based, in part, on the finding that the use of an NS4a/modified NS3 HCV polypeptide provides superior reagents for detecting HCV infection. The NS4a/modified NS3 polypeptides retain conformational epitopes and hence immunoreactivity, and can therefore be used alone or in combination with other HCV reagents for accurately and efficiently detecting the presence of HCV infection, particularly early detection of HCV-specific antibodies. The assays described herein may be used to detect HCV infection caused by any of the six known genotypes of HCV.

Accordingly, in one embodiment, the invention is directed to an immunoassay reagent comprising a polypeptide comprising a hepatitis C virus (HCV) NS4a domain having SEQ ID NO:3, a modified HCV NS3 domain having SEQ ID NO:4, wherein one or more amino acid residues of SEQ ID NO:4 are modified such that protease activity of the modified hepatitis C virus NS3 domain is inhibited relative to protease activity of the hepatitis C virus NS3 domain having SEQ ID NO:4 lacking the modifications, and an intervening region connecting the carboxy terminus of the NS4a domain to the amino terminus of the modified NS3 domain, or a polypeptide having at least 90% amino acid homology to such polypeptide, or a polypeptide having at least 90% amino acid identity to such polypeptide. The NS3 domain is modified relative to the native HCV NS3 domain in that amino acid residues 15 and 16 in SEQ ID NO:4 are lysine (K) instead of isoleucine (I). Preferably, the modification to inhibit protease activity comprises substitution of one or more of amino acid residues 55, 79 and 137 of SEQ ID NO:4, preferably a substitution of alanine or glycine. In a preferred embodiment, the modification to inhibit protease activity comprises substitution of alanine for amino acid residue 137 of SEQ ID NO:4.

In a preferred embodiment of the polypeptide of the subject invention, the intervening region is the amino acid triplet SGS, resulting in a polypeptide comprising, or more particularly consisting of, SEQ ID NO:2. The intervening region, preferably a tripeptide flexible linker, is termed a "turn" sequence. The turn sequence allows the NS4a domain to fold into the pocket within the protease region of the NS3 domain.

In further embodiments the immunoassay reagent of the subject invention is bound to a solid support.

In further embodiments, the invention is directed to a method of detecting antibodies to HCV in a biological sample. The method comprises: (a) providing an immunoassay reagent as described above; (b) combining a biological sample with the immunoassay reagent under conditions which allow HCV antibodies, when present in the biological sample, to bind to the polypeptide to form a first immune complex; (c) adding to the first immune complex from step (b) a labeled detector, wherein the labeled detector is reactive with the immune complex; and (d) detecting second immune complexes formed between the labeled detector and the first immune complex, if any, as an indication of the presence of HCV antibodies in the biological sample. Preferably, the labeled detector is an antibody or an antigen. Preferably, the immunoassay reagent is bound to a solid support.

In a further embodiment, the invention is directed to a method of detecting antibodies to hepatitis C virus and/or hepatitis C virus antigen (a "combination" or "combo" assay) in a biological sample. The method comprises: (a) providing an immunoassay reagent as described above; (b) combining a biological sample with the immunoassay reagent and one or more anti-HCV antibodies under conditions which allow HCV antibodies, when present in the biological sample, to bind to the polypeptide to form a first immune complex, and which further allow HCV antigens, when present in the biological sample, to bind to the anti-HCV antibodies to form a second immune complex; (c) adding to the first immune complex from step (b) a first labeled detector, wherein the first labeled detector is reactive with said first immune complex, and adding to the second immune complex from step (b) a second labeled detector, wherein the second labeled detector is reactive with the second immune complex; (d) detecting third immune complexes formed between the first labeled detector and the first immune complex, if any, and detecting fourth immune complexes formed between the second labeled detector and the second immune complex, if any, as an indication of the presence of antibodies to HCV and/or the presence of HCV antigens in the biological sample. Preferably, the first labeled detector and the second labeled detector are each labeled antibody or labeled antigen (in any combination thereof; i.e. both could be labeled antibody; both could be labeled antigen; one could be labeled antibody while the other is labeled antigen). Preferably, one or more of the immunoassay reagent and the one or more anti-HCV antibodies are bound to the same or different solid support.

In still further embodiments, the invention is directed to an immunodiagnostic test kit comprising an immunoassay reagent as described above, and instructions for conducting the immunodiagnostic test.

In an additional embodiment, the invention is directed to an immunodiagnostic test kit which further comprises one or more anti-HCV antibodies, preferably anti-HCV core antibody.

In additional embodiments, the invention is directed to an isolated polypeptide comprising the amino acid sequence of SEQ ID NO:2. In certain embodiments, the polypeptide consists of the amino acid sequence of SEQ ID NO:2.

In further embodiments, the invention provides a method of selecting biological samples from a supply of human biological samples comprising selecting from the supply those samples that comprise antibodies that form an antigen-antibody complex with the immunoassay reagent according to the subject invention. This is useful to identify an HCV positive sample for removal from the supply, particularly relevant when the supply is a blood supply. Those samples which are not selected can be employed for the preparation of blood-related products. By identifying an HCV positive sample, the method can also be useful in the enrichment of positive samples.

The invention further provides a method of selecting biological samples from a supply of human biological samples comprising selecting from the supply those samples that do not comprise antibodies that form an antigen-antibody complex with the immunoassay reagent according to the subject invention. This is useful to identify biological samples useful for the preparation of blood-related products.

These and other aspects of the present invention will become evident upon reference to the following detailed description and attached drawings. In addition, various references are set forth herein which describe in more detail certain procedures or compositions, and are therefore incorporated by reference in their entirety.

Additional features and advantages of the subject invention will be apparent from the description which follows when considered in conjunction with the attached figures.

BRIEF DESCRIPTION OF THE DRAWINGS

FIG. 1 is a diagrammatic representation of the HCV genome, depicting the various regions of the polyprotein from which the present assay reagents (proteins and antibodies) are derived.

DETAILED DESCRIPTION OF THE INVENTION

Figure 2:
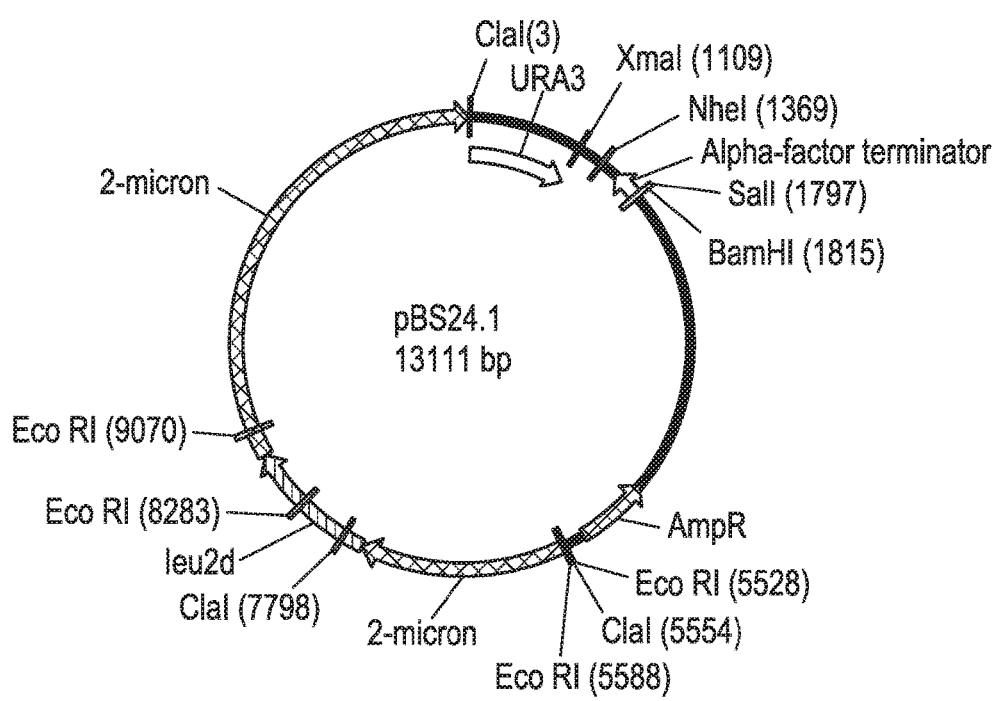
FIG. 2 is a circular map of the yeast expression vector pBS24.1.

The practice of the present invention will employ, unless otherwise indicated, conventional methods of chemistry, biochemistry, recombinant DNA techniques and immunology, within the skill of the art. Such techniques are explained fully in the literature. See, e.g., Fundamental Virology, 2nd Edition, vol. I & II (B. N. Fields and D. M. Knipe, eds.); Handbook of Experimental Immunology, Vols. I-IV (D. M. Weir and C. C. Blackwell eds., Blackwell Scientific Publications); T. E. Creighton, Proteins: Structures and Molecular Properties (W.H. Freeman and Company, 1993); A. L. Lehninger, Biochemistry (Worth Publishers, Inc., current addition); Sambrook, et al., Molecular Cloning: A Laboratory Manual (2nd Edition, 1989); Methods In Enzymology (S. Colowick and N. Kaplan eds., Academic Press, Inc.).

All publications, patents and patent applications cited herein, whether supra or infra, are hereby incorporated by reference in their entirety.

It must be noted that, as used in this specification and the appended claims, the singular forms "a", "an" and "the" include plural referents unless the content clearly dictates otherwise. Thus, for example, reference to "an antigen" includes a mixture of two or more antigens, and the like.

The following amino acid abbreviations are used throughout the text:

| | |
|---|---|
| Alanine: Ala (A) | Arginine: Arg (R) |
| Asparagine: Asn (N) | Aspartic acid: Asp (D) |
| Cysteine: Cys (C) | Glutamine: Gln (Q) |
| Glutamic acid: Glu (E) | Glycine: Gly (G) |
| Histidine: His (H) | Isoleucine: Ile (I) |
| Leucine: Leu (L) | Lysine: Lys (K) |
| Methionine: Met (M) | Phenylalanine: Phe (F) |
| Proline: Pro (P) | Serine: Ser (S) |
| Threonine: Thr (T) | Tryptophan: Trp (W) |
| Tyrosine: Tyr (Y) | Valine: Val (V) |

I. Definitions

In describing the present invention, the following terms will be employed, and are intended to be defined as indicated below.

The terms "polypeptide" and "protein" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include postexpression modifications of the polypeptide, for example, glycosylation, acetylation, phosphorylation and the like. Furthermore, for purposes of the present invention, a "polypeptide" refers to a protein which includes modifications, such as deletions, additions and substitutions (generally conservative in nature), to the native sequence, so long as the protein maintains the desired activity. These modifications may be deliberate, as through site-directed mutagenesis, or may be accidental, such as through mutations of hosts which produce the proteins or errors due to PCR amplification.

An HCV polypeptide is a polypeptide, as defined above, derived from the HCV polyprotein. The polypeptide need not be physically derived from HCV, but may be synthetically or recombinantly produced. Moreover, the polypeptide may be derived from any of the various HCV strains and isolates, such as, but not limited to, any of the isolates from strains 1, 2, 3, 4, 5 or 6 of HCV. A number of conserved and variable regions are known between these strains and, in general, the amino acid sequences of epitopes derived from these regions will have a high degree of sequence homology, e.g., amino acid sequence homology of more than 30%, preferably more than 40%, when the two sequences are aligned. Thus, for example, the term "NS4a/3" polypeptide refers to NS4a combined with NS3 from any of the various HCV strains, as well as NS4a/3 analogs, muteins and immunogenic fragments, as defined further below. The complete genotypes of many of these strains are known. See, e.g., U.S. Pat. No. 6,150,087 and GenBank Accession Nos. AJ238800 and AJ238799.

A polypeptide "derived from" an HCV polyprotein intends a polypeptide which comprises a sequence of one or more regions or portions of regions of the reference HCV polyprotein. Typically, the polypeptide is composed of regions or portions of regions that include epitopes, and will generally have an amino acid sequence substantially homologous to the reference polypeptide, as defined below. Thus, the term "derived from" is used to identify the original source of a molecule but is not meant to limit the method by which the molecule is made which can be, for example, by chemical synthesis or recombinant means.

The terms "analog" and "mutein" refer to biologically active derivatives of the reference molecule, or fragments of such derivatives, that retain desired activity, such as immunoreactivity in the assays described herein. In general, the term "analog" refers to compounds having a native polypeptide sequence and structure with one or more amino acid additions, substitutions (generally conservative in nature, or in the case of various embodiments of modified NS3, non-conservative in nature at the active proteolytic site) and/or deletions, relative to the native molecule, so long as the modifications do not destroy immunogenic activity. The term "mutein" refers to polypeptides having one or more amino acid-like molecules including but not limited to compounds comprising only amino and/or imino molecules, polypeptides containing one or more analogs of an amino acid (including, for example, unnatural amino acids, etc.), polypeptides with substituted linkages, as well as other modifications known in the art, both naturally occurring and non-naturally occurring (e.g., synthetic), cyclized, branched molecules and the like. The term also includes molecules comprising one or more N-substituted glycine residues (a "peptoid") and other synthetic amino acids or peptides. (See, e.g., U.S. Pat. Nos. 5,831,005; 5,877,278; and 5,977,301; Nguyen et al., Chem Biol. (2000) 7:463-473; and Simon et al., Proc. Natl. Acad. Sci. USA (1992) 89:9367-9371 for descriptions of peptoids). Preferably, the analog or mutein has at least the same immunoactivity as the native molecule. Methods for making polypeptide analogs and muteins are known in the art and are described further below.

As explained above, analogs generally include substitutions that are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. For example, the polypeptide of interest may include up to about 5-10 conservative or non-conservative amino acid substitutions, or even up to about 15-25 conservative or non-conservative amino acid substitutions, or any integer between 5-25, so long as the desired function of the molecule remains intact. One of skill in the art may readily determine regions of the molecule of interest that can tolerate change by reference to Hopp/Woods and Kyte-Doolittle plots, well known in the art.

By "modified NS3" is meant an NS3 polypeptide modified relative to the native HCV NS3 domain in that amino acid residues 15 and 16 in SEQ ID NO:4 are lysine (K) instead of isoleucine (I), and wherein one or more amino acid residues of SEQ ID NO:4 are modified such that protease activity of the modified hepatitis C virus NS3 domain is inhibited relative to protease activity of the hepatitis C virus NS3 domain having SEQ ID NO:4 lacking the modifications. Preferably, the modification to inhibit protease activity comprises substitution of one or more of amino acid residues 55, 79 and 137 of SEQ ID NO:4, preferably a substitution of alanine or glycine. In a preferred embodiment, the modification to inhibit protease activity comprises substitution of alanine for amino acid residue 137 of SEQ ID NO:4.

By "fragment" is intended a polypeptide consisting of only a part of the intact full-length polypeptide sequence and structure. The fragment can include a C-terminal deletion and/or an N-terminal deletion of the native polypeptide. An "immunogenic fragment" of a particular HCV protein will generally include at least about 5-10 contiguous amino acid residues of the full-length molecule, preferably at least about 15-25 contiguous amino acid residues of the full-length molecule, and most preferably at least about 20-50 or more contiguous amino acid residues of the full-length molecule, that define an epitope, or any integer between 5 amino acids and the full-length sequence, provided that the fragment in question retains immunoreactivity in the assays described herein.

The term "epitope" as used herein refers to a sequence of at least about 3 to 5, preferably about 5 to 10 or 15, and not more than about 1,000 amino acids (or any integer therebetween), which define a sequence that by itself or as part of a larger sequence, binds to an antibody generated in response to such sequence. There is no critical upper limit to the length of the fragment, which may comprise nearly the full-length of the protein sequence, or even a fusion protein comprising two or more epitopes from the HCV polyprotein. An epitope for use in the subject invention is not limited to a polypeptide having the exact sequence of the portion of the parent protein from which it is derived. Indeed, viral genomes are in a state of constant flux and contain several variable domains which exhibit relatively high degrees of variability between isolates. Thus the term "epitope" encompasses sequences identical to the native sequence, as well as modifications to the native sequence, such as deletions, additions and substitutions (generally conservative in nature).

Regions of a given polypeptide that include an epitope can be identified using any number of epitope mapping techniques, well known in the art. See, e.g., Epitope Mapping Protocols in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) Proc. Natl. Acad. Sci. USA 81:3998-4002; Geysen et al. (1985) Proc. Natl. Acad. Sci. USA 82:178-182; Geysen et al. (1986) Molec. Immunol. 23:709-715, all incorporated herein by reference in their entireties. Using such techniques, a number of epitopes of HCV have been identified. See, e.g., Chien et al., Viral Hepatitis and Liver Disease (1994) pp. 320-324, and further below. Similarly, conformational epitopes are readily identified by determining spatial conformation of amino acids such as by, e.g., x-ray crystallography and 2-dimensional nuclear magnetic resonance. See, e.g., Epitope Mapping Protocols, supra. Antigenic regions of proteins can also be identified using standard antigenicity and hydropathy plots, such as those calculated using, e.g., the Omiga version 1.0 software program available from the Oxford Molecular Group. This computer program employs the Hopp/Woods method, Hopp et al., Proc. Natl. Acad. Sci USA (1981) 78:3824-3828 for determining antigenicity profiles, and the Kyte-Doolittle technique, Kyte et al., J. Mol. Biol. (1982) 157:105-132 for hydropathy plots.

As used herein, the term "conformational epitope" refers to a portion of a full-length protein, or an analog or mutein thereof, having structural features native to the amino acid sequence encoding the epitope within the full-length natural protein. Native structural features include, but are not limited to, glycosylation and three dimensional structure. The length of the epitope-defining sequence can be subject to wide variations as these epitopes are believed to be formed by the three-dimensional shape of the antigen (e.g., folding). Thus, amino acids defining the epitope can be relatively few in number, but widely dispersed along the length of the molecule, being brought into correct epitope conformation via folding. The portions of the antigen between the residues defining the epitope may not be critical to the conformational structure of the epitope. For example, deletion or substitution of these intervening sequences may not affect the conformational epitope provided sequences critical to epitope conformation are maintained (e.g., cysteines involved in disulfide bonding, glycosylation sites, etc.).

Conformational epitopes present in the NS4a/3 region are readily identified using methods discussed above. Moreover, the presence or absence of a conformational epitope in a given polypeptide can be readily determined through screening the antigen of interest with an antibody (polyclonal serum or monoclonal to the conformational epitope) and comparing its reactivity to that of a denatured version of the antigen which retains only linear epitopes (if any). In such screening using polyclonal antibodies, it may be advantageous to absorb the polyclonal serum first with the denatured antigen and see if it retains antibodies to the antigen of interest.

Preferably, a conformational epitope is produced recombinantly and is expressed in a cell from which it is extractable under conditions which preserve its desired structural features, e.g. without denaturation of the epitope. Such cells include bacteria, yeast, insect, and mammalian cells. Expression and isolation of recombinant conformational epitopes from the HCV polyprotein are described in e.g., International Publication Nos. WO 96/04301, WO 94/01778, WO 95/33053, WO 92/08734, which applications are herein incorporated by reference in their entirety. Alternatively, it is possible to express the antigens and further renature the protein after recovery. It is also understood that chemical synthesis may also provide conformational antigen mimitopes that cross-react with the native antigen's conformational epitope.

An "antibody" ("Ab") intends a molecule that specifically binds to an epitope of interest present in an antigen. By "specifically binds" is meant that the antibody recognizes and interacts with the epitope in a "lock and key" type of interaction to form a complex between the antigen and antibody, as opposed to non-specific binding that might occur between the antibody and, for instance, the test substrate. Thus, for example, an HCV core antibody is a molecule that specifically binds to the HCV core protein. The term "antibody" as used herein includes antibodies obtained from both polyclonal and monoclonal preparations, as well as, the following: hybrid (chimeric) antibody molecules (see, for example, Winter et al. (1991) Nature 349: 293-299; and U.S. Pat. No. 4,816,567); F(ab')2 and F(ab) fragments; Fv molecules (non-covalent heterodimers, see, for example, Inbar et al. (1972) Proc Natl Acad Sci USA 69:2659-2662; and Ehrlich et al. (1980) Biochem 19:4091-4096); single-chain Fv molecules (sFv) (see, for example, Huston et al. (1988) Proc Natl Acad Sci USA 85:5879-5883); dimeric and trimeric antibody fragment constructs; minibodies (see, e.g., Pack et al. (1992) Biochem 31:1579-1584; Cumber et al. (1992) J Immunology 149B: 120-126); humanized antibody molecules (see, for example, Riechmann et al. (1988) Nature 332:323-327; Verhoeyan et al. (1988) Science 239:1534-1536; and U.K. Patent Publication No. GB 2,276,169, published 21 Sep. 1994); and, any functional fragments obtained from such molecules, wherein such fragments retain immunological binding properties of the parent antibody molecule.

As used herein, the term "monoclonal antibody" refers to an antibody composition having a homogeneous antibody population. The term is not limited regarding the species or source of the antibody, nor is it intended to be limited by the manner in which it is made. Thus, the term encompasses antibodies obtained from murine hybridomas, as well as human monoclonal antibodies obtained using human rather than murine hybridomas. See, e.g., Cote, et al. Monclonal Antibodies and Cancer Therapy, Alan R. Liss, 1985, p. 77.

By "isolated" is meant, when referring to a polypeptide, that the indicated molecule is separate and discrete from the whole organism with which the molecule is found in nature or is present in the substantial absence of other biological macro-molecules of the same type.

By "equivalent antigenic determinant" is meant an antigenic determinant from different sub-species or strains of HCV, such as from strains 1, 2, or 3 of HCV. More specifically, epitopes are known, such as "5-1-1", occurring at approximately positions 1694-1735, numbered relative to the HCV-1 polyprotein sequence (see SEQ ID NO:1), and such epitopes vary between the strains 1, 2, and 3. Thus, the epitope 5-1-1 from the three different strains are equivalent antigenic determinants and therefore are "copies" even though their sequences are not identical. In general the amino acid sequences of equivalent antigenic determinants will have a high degree of sequence homology, e.g., amino acid sequence homology of more than 30%, preferably more than 40%, when the two sequences are aligned.

"Homology" refers to the percent similarity between two polynucleotide or two polypeptide moieties. Two DNA, or two polypeptide sequences are "substantially homologous" to each other when the sequences exhibit at least about 50%, preferably at least about 75%, more preferably at least about 80%-85%, preferably at least about 90%, and most preferably at least about 95%-98% sequence similarity over a defined length of the molecules. As used herein, substantially homologous also refers to sequences showing complete identity to the specified DNA or polypeptide sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules (the reference sequence and a sequence with unknown % identity to the reference sequence) by aligning the sequences, counting the exact number of matches between the two aligned sequences, dividing by the length of the reference sequence, and multiplying the result by 100.

Readily available computer programs can be used to aid in the analysis of homology and identity, such as ALIGN, Dayhoff, M. O. in Atlas of Protein Sequence and Structure M. O. Dayhoff ed., 5 Suppl. 3:353-358, National biomedical Research Foundation, Washington, D.C., which adapts the local homology algorithm of Smith and Waterman Advances in Appl. Math. 2:482-489, 1981 for peptide analysis. Programs for determining nucleotide sequence homology are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent homology of a particular nucleotide sequence to a reference sequence can be determined using the homology algorithm of Smith and Waterman with a default scoring table and a gap penalty of six nucleotide positions.

Another method of establishing percent homology in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence homology." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs are readily available.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; DNA Cloning, supra; Nucleic Acid Hybridization, supra.

A "coding sequence" or a sequence which "encodes" a selected polypeptide, is a nucleic acid molecule which is transcribed (in the case of DNA) and translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A transcription termination sequence may be located 3' to the coding sequence.

"Operably linked" refers to an arrangement of elements wherein the components so described are configured so as to perform their desired function. Thus, a given promoter operably linked to a coding sequence is capable of effecting the expression of the coding sequence when the proper transcription factors, etc., are present. The promoter need not be contiguous with the coding sequence, so long as it functions to direct the expression thereof. Thus, for example, intervening untranslated yet transcribed sequences can be present between the promoter sequence and the coding sequence, as can transcribed introns, and the promoter sequence can still be considered "operably linked" to the coding sequence.

"Recombinant" as used herein to describe a nucleic acid molecule means a polynucleotide of genomic, cDNA, viral, semisynthetic, or synthetic origin which, by virtue of its origin or manipulation is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

A "control element" refers to a polynucleotide sequence which aids in the expression of a coding sequence to which it is linked. The term includes promoters, transcription termination sequences, upstream regulatory domains, polyadenylation signals, untranslated regions, including 5'-UTRs and 3'-UTRs and when appropriate, leader sequences and enhancers, which collectively provide for the transcription and translation of a coding sequence in a host cell.

A "promoter" as used herein is a DNA regulatory region capable of binding RNA polymerase in a host cell and initiating transcription of a downstream (3' direction) coding sequence operably linked thereto. For purposes of the present invention, a promoter sequence includes the minimum number of bases or elements necessary to initiate transcription of a gene of interest at levels detectable above background. Within the promoter sequence is a transcription initiation site, as well as protein binding domains (consensus sequences) responsible for the binding of RNA polymerase. Eucaryotic promoters will often, but not always, contain "TATA" boxes and "CAT" boxes.

A control sequence "directs the transcription" of a coding sequence in a cell when RNA polymerase will bind the promoter sequence and transcribe the coding sequence into mRNA, which is then translated into the polypeptide encoded by the coding sequence.

"Expression cassette" or "expression construct" refers to an assembly which is capable of directing the expression of the sequence(s) or gene(s) of interest. The expression cassette includes control elements, as described above, such as a promoter which is operably linked to (so as to direct transcription of) the sequence(s) or gene(s) of interest, and often includes a polyadenylation sequence as well. Within certain embodiments of the invention, the expression cassette described herein may be contained within a plasmid construct. In addition to the components of the expression cassette, the plasmid construct may also include, one or more selectable markers, a signal which allows the plasmid construct to exist as single-stranded DNA (e.g., a M13 origin of replication), at least one multiple cloning site, and a "mammalian" origin of replication (e.g., a SV40 or adenovirus origin of replication).

"Transformation," as used herein, refers to the insertion of an exogenous polynucleotide into a host cell, irrespective of the method used for insertion: for example, transformation by direct uptake, transfection, infection, and the like. For particular methods of transfection, see further below. The exogenous polynucleotide may be maintained as a nonintegrated vector, for example, an episome, or alternatively, may be integrated into the host genome.

A "host cell" is a cell which has been transformed, or is capable of transformation, by an exogenous DNA sequence.

As used herein, a "biological sample" refers to a sample of tissue or fluid isolated from a subject, that commonly includes antibodies produced by the subject or antigens present in the subject. Typical samples that include such antibodies and/or antigens are known in the art and include but not limited to, blood, plasma, serum, fecal matter, urine, bone marrow, bile, spinal fluid, lymph fluid, samples of the skin, secretions of the skin, respiratory, intestinal, and genitourinary tracts, tears, saliva, milk, blood cells, organs, biopsies and also samples of in vitro cell culture constituents including but not limited to conditioned media resulting from the growth of cells and tissues in culture medium, e.g., recombinant cells, and cell components.

"Solid support" intends a solid matrix to which the HCV polypeptides used in the subject immunoassays (and/or the HCV antigens in the combination assays of the subject invention) are bound covalently or by noncovalent means such as hydrophobic adsorption.

"Immunologically reactive" or "immunoreactive" means that the antigen in question will react specifically with anti-HCV antibodies present in a biological sample from an HCV-infected individual, and/or that the anti-HCV antibodies in question will react specifically with HCV antigen present in a biological sample from an HCV-infected individual.

"Immunogenic" intends that the antigen is question will elicit an immune reaction when administered to an individual.

"Immune complex" intends the combination formed when an antibody binds to an epitope on an antigen.

As used herein, the terms "label" and "detectable label" refer to a molecule capable of detection, including, but not limited to, radioactive isotopes, fluorescers, chemiluminescers, chromophores, enzymes, enzyme substrates, enzyme cofactors, enzyme inhibitors, chromophores, dyes, metal ions, metal sols, ligands (e.g., biotin, avidin, strepavidin or haptens) and the like. The term "fluorescer" refers to a substance or a portion thereof which is capable of exhibiting fluorescence in the detectable range. Particular examples of labels which may be used under the invention include, but are not limited to, horse radish peroxidase (HRP), fluorescein, FITC, rhodamine, dansyl, umbelliferone, dimethyl acridinium ester (DMAE), Texas red, luminol, NADPH and .alpha.-.beta.-galactosidase.

II. Modes of Carrying Out the Invention

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of compositions and methods similar or equivalent to those described herein can be used in the practice of the present invention, the preferred materials and methods are described herein.

As noted above, the present invention is based on the discovery that the use of an NS4a/modified NS3 HCV polypeptide provides superior reagents for detecting HCV infection. The NS4a/modified NS3 polypeptides retain conformation epitopes and hence immunoreactivity, and can therefore be used alone or in combination with other HCV reagents for accurately and efficiently detecting the presence of HCV infection. The assays described herein may be used to detect HCV infection caused by any of the six known genotypes of HCV. The NS4a/modified NS3 polypeptides are especially useful in diagnostic methods for accurately detecting early HCV infection. The methods can be used to detect HCV infection during the early stages of HCV seroconversion, thereby increasing detection accuracy and reducing the incidence of false results.

The NS4a/modified NS3 polypeptides can be used alone in immunoassays or in combination with other HCV antigens, either from the same or different HCV genotypes and isolates, for example, major epitopes of HCV core, E1, E2, NS3, 5-1-1, c100-3 and NS5 sequences. The methods can be conveniently practiced in a single assay, using any of the several assay formats described below, such as but not limited to, assay formats which utilize a solid support to which the HCV antigens (and/or anti-HCV antibodies) are bound.

In order to further an understanding of the invention, a more detailed discussion is provided below regarding NS4a/modified NS3 polypeptides, as well as production of the proteins, and methods of using the proteins.

HCV Proteins

The genomes of HCV strains contain a single open reading frame of approximately 9,000 to 12,000 nucleotides, which is transcribed into a polyprotein. As shown in FIG. 1 and Table 1, an HCV polyprotein, upon cleavage, produces at least ten distinct products, in the following order: $NH_2$-Core-E1-E2-p7-NS2-NS3-NS4a-NS4b-NS5a-NS5b-COOH. The core polypeptide occurs at positions 1-191 of SEQ ID NO:1, numbered relative to HCV-1 (see, Choo et al. (1991) Proc. Natl. Acad. Sci. USA 88:2451-2455, for the HCV-1 genome). This polypeptide is further processed to produce an HCV polypeptide with approximately amino acids 1-173 of SEQ ID NO:1. The envelope polypeptides, E1 and E2, occur at about positions 192-383 of SEQ ID NO:1 and 384-746 of SEQ ID NO:1, respectively. The P7 domain is found at about positions 747-809 of SEQ ID NO:1. NS2 is an integral membrane protein with proteolytic activity and is found at about positions 810-1026 of SEQ ID NO:1 of the polyprotein. NS2, in combination with NS3 (found at about positions 1027-1657 of SEQ ID NO:1), cleaves the NS2-NS3 sissle bond which in turn generates the NS3 N-terminus and releases a large polyprotein that includes both serine protease and RNA helicase activities. The NS3 protease, found at about positions 1027-1207 of SEQ ID NO:1, serves to process the remaining polyprotein. The helicase activity is found at about positions 1193-1657 of SEQ ID NO:1. NS3 liberates an NS3 cofactor (NS4a, found about positions 1658-1711 of SEQ ID NO:1), two proteins (NS4b found at about positions 1712-1972 of SEQ ID NO:1, and NS5a found at about positions 1973-2420 of SEQ ID NO:1), and an RNA-dependent RNA polymerase (NS5b found at about positions 2421-3011 of SEQ ID NO:1). Completion of polyprotein maturation is initiated by autocatalytic cleavage at the NS3-NS4a junction, catalyzed by the NS3 serine protease.

The modified NS3 polypeptides of the invention are mutated relative to the native HCV NS3 domain in that amino acid residues 15 and 16 in SEQ ID NO:4 are lysine (K) instead of isoleucine (I). This substitution of hydrophilic amino acid residues for hydrophobic amino acid residues produces a more soluble and stable form of immunoassay reagent in accordance with the subject invention.

The modified NS3 polypeptides of the invention are also mutated to inhibit protease activity, such that further cleavage of a polypeptide including the modified NS3 domain, such as an NS4a/3 polypeptide, as well as catalytic cleavage of additional HCV proteins used in combination with the modified NS3 polypeptide, is inhibited. The NS3 polypeptide can be modified by deletion of all or a portion of the NS3 protease domain. Alternatively, proteolytic activity can be inhibited by substitution of amino acids within active regions of the protease domain. Finally, additions of amino acids to active regions of the domain, such that the catalytic site is modified, will also serve to inhibit proteolytic activity. Preferably, the modifications made to reduce or eliminate protease activity do not disrupt the conformational epitopes in the native NS3 or NS4a/3 proteins.

As explained above, the protease activity is found at about amino acid positions 1027-1207 of SEQ ID NO:1, numbered relative to the full-length HCV-1 polyprotein (see, Choo et al., Proc. Natl. Acad. Sci. USA (1991) 88:2451-2455). The structure of the NS3 protease and active site are known. See, e.g., Lin, "HCV NS3-4A Serine Proteases" in "Hepatitis C Viruses: Genomes and Molecular Biology", Ed. S. L. Tan, Horizon Bioscience (2006); Kim et al., Cell (1996) 87:343-355; Tomei et al., J Virology (1993) 67(7):4017-4026; De Francesco et al., Antivir. Ther. (1998) 3:99-109; Koch et al., Biochemistry (2001) 40:631-640. Thus, deletions or modifications to the native sequence will typically occur at or near the active site of the molecule. Preferred modifications are to the catalytic triad at the active site of the protease, i.e., H, D and/or S residues, in order to inactivate the protease. These residues occur at positions $His^{1083}$, $Asp^{1107}$, and $Ser^{1165}$ of the catalytic triad in SEQ ID NO:1, respectively, numbered relative to the full-length HCV polyprotein (positions 55, 79 and 137, respectively, of SEQ ID NO:4). Such modifications will suppress proteolytic cleavage activity of the NS3 protease while maintaining immunoreactivity. Particularly preferred substitutions are non-conservative in nature and neutral, such as a substitution of Ala or Glycine for one or more of the amino acid residues normally found at positions 1083, 1107 and 1165 of SEQ ID NO:1 of the protease domain (positions 55, 79 and 137, respectively, of SEQ ID NO:4). One of skill in the art can readily determine portions of the NS3 protease to delete in order to disrupt activity.

Moreover, other appropriate amino acid modifications at these sites can be readily determined by one of skill in the art based on the known structure and function of the HCV NS3 protease as described in e.g., De Francesco et al., Antivir. Ther. (1998) 3 (Suppl 3):99-109; and Schechter and Berger, Biochim. Biophys. Res. Commun. (1967) 27:157-162. In particular, it is known that NS3 protease is a serine protease and the proteolytic mechanism is based on nucleophilic attack of the targeted peptidic bond by a serine. In many cases the nucleophilic property of the group is improved by the presence of a histidine, held in a "proton acceptor state" by an aspartate. Aligned side chains of serine, histidine and aspartate build the catalytic triad common to most serine proteases. The active site of serine proteases is shaped as a cleft where the polypeptide substrate binds. Schechter and Berger, Biochim. Biophys. Res. Commun. (1967) 27:157-162 labeled amino acid residues from N to C terminus of the polypeptide substrate (Pi, . . . , P3, P2, P1, P1', P2', P3', . . . , Pj) and their respective binding subsites (Si, . . . , S3, S2, 51, SP, S2', S3', . . . , Sj) and found the cleavage is catalyzed between P1 and P1'. The NS3 protease adopts a chymotrypsin-like fold and includes a very long, solvent exposed substrate-binding site, consistent with the requirement for very long peptide substrates (P6-P4'). The NS3 protease has a preference for cysteine residues in the substrate P1 position. Thus, based on the known structure and function as described above and in the art, one of skill in the art can readily determine other amino acid substitutions, additions and deletions that will serve to disrupt the proteolytic activity of NS3 protease.

The presence or absence of NS3 proteolytic activity can be determined using methods known to those of skill in the art. For example, protease activity or lack thereof may be determined using the procedure described below in the examples, as well as using assays well known in the art. See, e.g., Takeshita et al., Anal. Biochem. (1997) 247:242-246; Kakiuchi et al., J. Biochem. (1997) 122:749-755; Sali et al., Biochemistry (1998) 37:3392-3401; Cho et al., J. Virol. Meth. (1998) 72:109-115; Cerretani et al., Anal. Biochem. (1999) 266:192-197; Zhang et al., Anal. Biochem. (1999) 270:268-275; Kakiuchi et al., J. Virol. Meth. (1999) 80:77-84; Fowler et al., J. Biomol. Screen. (2000) 5:153-158; and Kim et al., Anal. Biochem. (2000) 284:42-48.

Nucleic acid and amino acid sequences of a number of HCV strains and isolates, including nucleic acid and amino acid sequences of the various regions of the HCV polyprotein, including Core, NS2, p'7, E1, E2, NS3, NS4a, NS4b, NS5a, NS5b genes and polypeptides have been determined. For example, isolate HCV J1.1 is described in Kubo et al. (1989) Japan. Nucl. Acids Res. 17:10367-10372; Takeuchi et al. (1990) Gene 91:287-291; Takeuchi et al. (1990) J. Gen. Virol. 71:3027-3033; and Takeuchi et al. (1990) Nucl. Acids Res. 18:4626. The complete coding sequences of two independent isolates, HCV-J and BK, are described by Kato et al., (1990) Proc. Natl. Acad. Sci. USA 87:9524-9528 and Takamizawa et al., (1991) J. Virol. 65:1105-1113 respectively.

Publications that describe HCV-1 isolates include Choo et al. (1990) Brit. Med. Bull. 46:423-441; Choo et al. (1991) Proc. Natl. Acad. Sci. USA 88:2451-2455 and Han et al. (1991) Proc. Natl. Acad. Sci. USA 88:1711-1715. HCV isolates HC-J1 and HC-J4 are described in Okamoto et al. (1991) Japan J. Exp. Med. 60:167-177. HCV isolates HCT 18.about., HCT 23, Th, HCT 27, EC1 and EC10 are described in Weiner et al. (1991) Virol. 180:842-848. HCV isolates Pt-1, HCV-K1 and HCV-K2 are described in Enomoto et al. (1990) Biochem. Biophys. Res. Commun. 170: 1021-1025. HCV isolates A, C, D & E are described in Tsukiyama-Kohara et al. (1991) Virus Genes 5:243-254.

The amino acid sequence of an NS4a/modified NS3 polypeptide in accordance with the subject invention is shown in SEQ ID NO:2. The sequence includes, in N-terminal to C-terminal direction, an N-terminal Met, amino acids 2-14 are NS4a, followed by intervening amino acids SGS, followed by amino acids 18-646 which are modified NS3 (amino acids 32 and 33 are lysine and amino acid 154 is alanine).

Anti-HCV Antibodies

Anti-HCV antibodies (directed against the same or different HCV domain epitopes) can include, for example, HCV anti-core antibodies. Examples of particular anti-core antibodies useful in the present invention include, but are not limited to, antibody molecules such as monoclonal antibodies, directed against epitopes in the core region found between amino acids 10-53 of SEQ ID NO:1, amino acids 10-45 of SEQ ID NO:1, amino acids 67-88 of SEQ ID NO:1, amino acids 120-130 of SEQ ID NO:1, or antibodies directed against any of the core epitopes identified in, e.g., U.S. Pat. No. 6,630,298; U.S. Pat. No. 6,150,087; U.S. Pat. No. 6,346,375; Houghton et al., U.S. Pat. No. 5,350,671; Chien et al., Proc. Natl. Acad. Sci. USA (1992) 89:10011-10015; Chien et al., J. Gastroent. Hepatol. (1993) 8:S33-39; Chien et al., International Publication No. WO 93/00365; and Chien, D. Y., International Publication No. WO 94/01778, the disclosures of which are incorporated herein by reference in their entireties.

Figure 6:
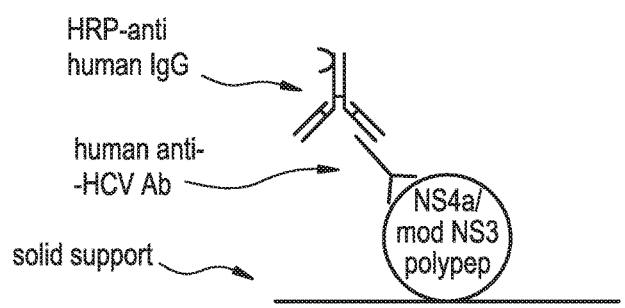
FIG. 6 is a schematic drawing of a representative immunoassay using an immunoassay reagent according to the subject invention where the immunoassay reagent is immobilized on a solid support.

In one embodiment of the invention, depicted in FIG. 6, a rapid capture ligand immunoassay is performed using a NS4a/modified NS3 polypeptide. The sample is combined with the antigens, which may be present on a solid support, as described further below. If the sample is infected with HCV, HCV antibodies to those epitopes present on the solid support will bind to the solid support components. Detection is by the attachment of a detectable marker (such as horse radish peroxidase (HRP) as shown in FIG. 6) to a member of the antigen/antibody complex. Attachment may be by covalent means or by subsequent binding of detectably labeled antibodies, such as in a standard sandwich assay, or by enzyme reaction, the product of which reaction is detectable. The detectable marker may include, but is not limited to, a chromophore, an antibody, an antigen, an enzyme, an enzyme reactive compound whose cleavage product is detectable, rhodamine or rhodamine derivative, biotin, avidin, strepavidin, a fluorescent compound, a chemiluminescent compound, such as dimethyl acridinium ester (DMAE), derivatives and/or combinations of these markers. A detectably labeled anti-human antibody, capable of detecting a human IgG molecule present, can be conveniently used.

Figure 7:
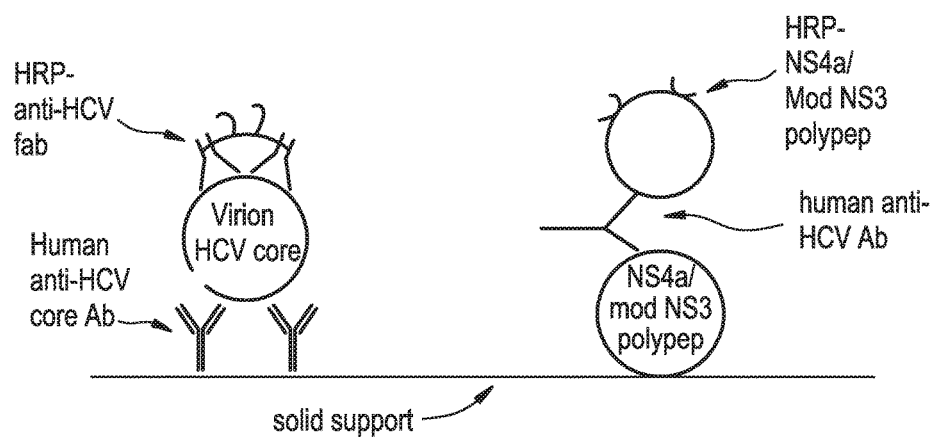
FIG. 7 is a schematic drawing of a representative immunoassay using immunoassay reagent and anti-HCV antibody according to the subject invention where immunoassay reagent and anti-HCV antibody are immobilized on a solid support.

In a further embodiment of the invention, depicted in FIG. 7, a rapid capture ligand immunoassay is performed using a NS4a/modified NS3 polypeptide and anti-HCVantibody. The sample is combined with the polypeptide and anti-HCV antibody, which may be present on a solid support, as described further below. If the sample is infected with HCV, HCV antibodies to those epitopes present on the solid support will bind to the solid support components, and HCV antigen immunologically reactive with the antibody epitopes on the solid support will also bind to the solid support components. Detection is by the attachment of a detectable marker (such as horse radish peroxidase (HRP) as shown in FIG. 7) to a member of the antigen/antibody complex. Attachment may be by covalent means or by subsequent binding of detectably labeled antibodies, such as in a standard sandwich assay, or by enzyme reaction, the product of which reaction is detectable. The detectable marker may include, but is not limited to, a chromophore, an antibody, an antigen, an enzyme, an enzyme reactive compound whose cleavage product is detectable, rhodamine or rhodamine derivative, biotin, avidin, strepavidin, a fluorescent compound, a chemiluminescent compound, such as dimethyl acridinium ester (DMAE), derivatives and/or combinations of these markers. A detectably labeled anti-human antibody, capable of detecting a human IgG molecule present, can be conveniently used.

Such an assay is an HCV combination assay, capable of detecting both HCV antigen and HCV antibody which may be present in a biological sample of an individual infected with HCV.

Production of HCV Antigens

As explained above, the molecules of the present invention are generally produced recombinantly. Thus, polynucleotides encoding HCV antigens for use with the present invention can be made using standard techniques of molecular biology. For example, polynucleotide sequences coding for the above-described molecules can be obtained using recombinant methods, such as by screening cDNA and genomic libraries from cells expressing the gene, or by deriving the gene from a vector known to include the same. Furthermore, the desired gene can be isolated directly from viral nucleic acid molecules, using techniques described in the art, such as in Houghton et al., U.S. Pat. No. 5,350,671. The gene of interest can also be produced synthetically, rather than cloned. The molecules can be designed with appropriate codons for the particular sequence. The complete sequence is then assembled from overlapping oligonucleotides prepared by standard methods and assembled into a complete coding sequence. See, e.g., Edge (1981) Nature 292:756; Nambair et al. (1984) Science 223:1299; and Jay et al. (1984) J. Biol. Chem. 259:6311.

Thus, particular nucleotide sequences can be obtained from vectors harboring the desired sequences or synthesized completely or in part using various oligonucleotide synthesis techniques known in the art, such as site-directed mutagenesis and polymerase chain reaction (PCR) techniques where appropriate. See, e.g., Sambrook, supra. In particular, one method of obtaining nucleotide sequences encoding the desired sequences is by annealing complementary sets of overlapping synthetic oligonucleotides produced in a conventional, automated polynucleotide synthesizer, followed by ligation with an appropriate DNA ligase and amplification of the ligated nucleotide sequence via PVR. See, e.g., Jayaraman et al. (1991) Proc. Natl. Acad. Sci. USA 88:4084-4088. Additionally, oligonucleotide directed synthesis (Jones et al. (1986) Nature 54:75-82), oligonucleotide directed mutagenesis of pre-existing nucleotide regions (Riechmann et al. (1988) Nature 332:323-327 and Verhoeyen et al. (1988) Science 239:1534-1536), and enzymatic filling-in of gapped oligonucleotides using T.sub.4 DNA polymerase (Queen et al. (1989) Proc. Natl. Acad. Sci. USA 86:10029-10033) can be used under the invention to provide molecules having altered or enhanced antigen-binding capabilities, and/or reduced immunogenicity.

Methods for producing mutants or analogs of the desired nucleotide sequence, such as NS3, or other HCV antigens, are well known. See, e.g., Dasmahapatra et al., U.S. Pat. No. 5,843,752 and Zhang et al., U.S. Pat. No. 5,990,276. Modified NS3 and other HCV proteins for use in immunoassays may be prepared by deletion of a portion of the sequence encoding the polypeptide of interest, by insertion of a sequence, and/or by substitution of one or more nucleotides within the sequence. Techniques for modifying nucleotide sequences, such as site-directed mutagenesis, and the like, are well known to those skilled in the art. See, e.g., Sambrook et al., supra; Kunkel, T. A. (1985) Proc. Natl. Acad. Sci. USA (1985) 82:448; Geisselsoder et al. (1987) BioTechniques 5:786; Zoller and Smith (1983) Methods Enzymol. 100:468; Dalbie-McFarland et al. (1982) Proc. Natl. Acad. Sci USA 79:6409.

Once coding sequences have been prepared or isolated, such sequences can be cloned into any suitable vector or replicon. Numerous cloning vectors are known to those of skill in the art, and the selection of an appropriate cloning vector is a matter of choice. Suitable vectors include, but are not limited to, plasmids, phages, transposons, cosmids, chromosomes or viruses which are capable of replication when associated with the proper control elements.

The coding sequence is then placed under the control of suitable control elements, depending on the system to be used for expression. Thus, the coding sequence can be placed under the control of a promoter, ribosome binding site (for bacterial expression) and, optionally, an operator, so that the DNA sequence of interest is transcribed into RNA by a suitable transformant. The coding sequence may or may not contain a signal peptide or leader sequence which can later be removed by the host in post-translational processing. See, e.g., U.S. Pat. Nos. 4,431,739; 4,425,437; 4,338,397.

In addition to control sequences, it may be desirable to add regulatory sequences which allow for regulation of the expression of the sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector. For example, enhancer elements may be used herein to increase expression levels of the constructs. Examples include the SV40 early gene enhancer (Dijkema et al. (1985) EMBO J. 4:761), the enhancer/promoter derived from the long terminal repeat (LTR) of the Rous Sarcoma Virus (Gorman et al. (1982) Proc. Natl. Acad. Sci. USA 79:6777) and elements derived from human CMV (Boshart et al. (1985) Cell 41:521), such as elements included in the CMV intron A sequence (U.S. Pat. No. 5,688,688). The expression cassette may further include an origin of replication for autonomous replication in a suitable host cell, one or more selectable markers, one or more restriction sites, a potential for high copy number and a strong promoter.

An expression vector is constructed so that the particular coding sequence is located in the vector with the appropriate regulatory sequences, the positioning and orientation of the coding sequence with respect to the control sequences being such that the coding sequence is transcribed under the "control" of the control sequences (i.e., RNA polymerase which binds to the DNA molecule at the control sequences transcribes the coding sequence). Modification of the sequences encoding the molecule of interest may be desirable to achieve this end. For example, in some cases it may be necessary to modify the sequence so that it can be attached to the control sequences in the appropriate orientation; i.e., to maintain the reading frame. The control sequences and other regulatory sequences may be ligated to the coding sequence prior to insertion into a vector. Alternatively, the coding sequence can be cloned directly into an expression vector which already contains the control sequences and an appropriate restriction site.

The molecules can be expressed in a wide variety of systems, including insect, mammalian, bacterial, viral and yeast expression systems, all well known in the art. For example, insect cell expression systems, such as baculovirus systems, are known to those of skill in the art and described in, e.g., Summers and Smith, Texas Agricultural Experiment Station Bulletin No. 1555 (1987). Materials and methods for baculovirus/insect cell expression systems are commercially available in kit form from, inter alia, Invitrogen, San Diego Calif. ("MaxBac" kit). Similarly, bacterial and mammalian cell expression systems are well known in the art and described in, e.g., Sambrook et al., supra. Yeast expression systems are also known in the art and described in, e.g., Yeast Genetic Engineering (Barr et al., eds., 1989) Butterworths, London.

A number of appropriate host cells for use with the above systems are also known. For example, mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human embryonic kidney cells, human hepatocellular carcinoma cells (e.g., Hep G2), Madin-Darby bovine kidney ("MDBK") cells, as well as others. Similarly, bacterial hosts such as *E. coli, Bacillus subtilis*, and *Streptococcus* spp., will find use with the present expression constructs. Yeast hosts useful in the present invention include inter alia, *Saccharomyces cerevisiae, Candida albicans, Candida maltosa, Hansenula polymorpha, Kluyveromyces fragilis, Kluyveromyces lactis, Pichia guillerimondii, Pichia pastoris, Schizosaccharomyces pombe* and *Yarrowia lipolytica*. Insect cells for use with baculovirus expression vectors include, inter alia, *Aedes aegypti, Autographa californica, Bombyx mori, Drosophila melanogaster, Spodoptera frugiperda*, and *Trichoplusia ni*.

Nucleic acid molecules comprising nucleotide sequences of interest can be stably integrated into a host cell genome or maintained on a stable episomal element in a suitable host cell using various gene delivery techniques well known in the art. See, e.g., U.S. Pat. No. 5,399,346.

Depending on the expression system and host selected, the molecules are produced by growing host cells transformed by an expression vector described above under conditions whereby the protein is expressed. The expressed protein is then isolated from the host cells and purified. If the expression system secretes the protein into growth media, the product can be purified directly from the media. If it is not secreted, it can be isolated from cell lysates. The selection of the appropriate growth conditions and recovery methods are within the skill of the art.

The recombinant production of various HCV antigens has been described. See, e.g., International Publication Nos. WO 94/01778, WO 93/00365, WO 04/00547 and WO 01/38360; U.S. Pat. Nos. 5,350,671, 5,683,864, 6,346,375, 6,150,087, 6,514,731, 6,428,792 and 6,632,601; Chien et al., J. Gastroent. Hepatol. (1993) 8:S33-39; Chien, D. Y., International Publication No. WO 94/01778; Chien et al., Proc. Natl. Acad. Sci. USA (1992) 89:10011-10015; the disclosures of all of which are incorporated herein by reference in their entireties. A preferred method of producing NS4a/modified NS3 polypeptides is described below.

Immunodiagnostic Assays

Once produced, the HCV antigens may be used in virtually any assay format that employs a known antigen to detect antibodies. A common feature of all of these assays is that the antigen is contacted with the biological sample suspected of containing HCV antibodies under conditions that permit the antigen to bind to any such antibodies present in the sample. Such conditions will typically be physiologic temperature, pH and ionic strength using an excess of antigen. The incubation of the antigen with the specimen is followed by detection of immune complexes comprised of the antigen.

Design of the immunoassays is subject to a great deal of variation, and many formats are known in the art. Protocols may, for example, use solid supports, or immunoprecipitation. Most assays involve the use of labeled antibody or polypeptide; the labels may be, for example, enzymatic, fluorescent, chemiluminescent, radioactive, or dye molecules, as discussed in detail above. Assays which amplify the signals from the immune complex are also known; examples of which are assays which utilize biotin and avidin, and enzyme-labeled and mediated immunoassays, such as ELISA assays.

The immunoassay may be, without limitation, a heterogenous or a homogeneous format, and of a standard or competitive type. In a heterogeneous format, the polypeptide is typically bound to a solid matrix or support to facilitate separation of the sample from the polypeptide after incubation. A solid support, for the purposes of this invention, can be any material that is an insoluble matrix and can have a rigid or semi-rigid surface. Exemplary solid supports include, but are not limited to, substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, and the like. Particular supports include plates, pellets, disks, capillaries, hollow fibers, needles, pins, solid fibers, cellulose beads, pore-glass beads, silica gels, polystyrene beads optionally cross-linked with divinylbenzene, grafted co-poly beads, polyacrylamide beads, latex beads, dimethylacrylamide beads optionally crosslinked with N—N'-bis-acryloylethylenediamine, and glass particles coated with a hydrophobic polymer.

If desired, the molecules to be added to the solid support can readily be functionalized to create styrene or acrylate moieties, thus enabling the incorporation of the molecules into polystyrene, polyacrylate or other polymers such as polyimide, polyacrylamide, polyethylene, polyvinyl, polydiacetylene, polyphenylene-vinylene, polypeptide, polysaccharide, polysulfone, polypyrrole, polyimidazole, polythiophene, polyether, epoxies, silica glass, silica gel, siloxane, polyphosphate, hydrogel, agarose, cellulose, and the like.

If more than one HCV antigen is used in the assays, for example, an NS4a/modified NS3 polypeptide and another HCV antigen, the antigens can be provided on the same solid substrate or on different solid substrates that are combined in the assay. Thus, for example, the antigens can be present as discrete entities on, e.g., a plate, or can be present on, for example, individual microbeads that are added together for use in the assay of interest.

In one context, as depicted in FIG. 6, a solid support is first reacted with the HCV antigens such as a NS4a/modified NS3 polypeptide (collectively called "the solid-phase components" herein), under suitable binding conditions such that the molecules are sufficiently immobilized to the support. Sometimes, immobilization to the support can be enhanced by first coupling the antigen to a protein with better solid phase-binding properties. Suitable coupling proteins include, but are not limited to, macromolecules such as serum albumins including bovine serum albumin (BSA), keyhole limpet hemocyanin, immunoglobulin molecules, thyroglobulin, ovalbumin, and other proteins well known to those skilled in the art. Other reagents that can be used to bind molecules to the support include polysaccharides, polylactic acids, polyglycolic acids, polymeric amino acids, amino acid copolymers, and the like. Such molecules and methods of coupling these molecules to antigens, are well known to those of ordinary skill in the art. See, e.g., Brinkley, M. A. (1992) Bioconjugate Chem. 3:2-13; Hashida et al. (1984) J. Appl. Biochem. 6:56-63; and Anjaneyulu and Staros (1987) International J. of Peptide and Protein Res. 30:117-124.

After reacting the solid support with the solid-phase components, any nonimmobilized solid-phase components are removed from the support by washing, and the support-bound components are then contacted with a biological sample suspected of containing HCV antibodies (collectively called "ligand molecules" herein) under suitable binding conditions. If HCV antibodies are present in the sample, they will form a complex with the HCV antigens. After washing to remove any nonbound ligand molecules, detectably labeled antibodies, such as anti-xenogenic (e.g., anti-human) antibodies, which recognize an epitope on anti-HCV antibodies, are added. These antibodies bind due to complex formation.

In a further assay format, well known in the art, a streptavidin-coated solid support is reacted with biotin labeled antibodies that bind the modified NS3. The biological sample is added under suitable binding conditions. If HCV antibodies are present in the sample, they will form a complex with the HCV antigens. After washing to remove any nonbound ligand molecules, detectably labeled antibodies are added, as described above.

In a homogeneous format, the test sample is incubated with the combination of antigens in solution. For example, it may be under conditions that will precipitate any antigen-antibody complexes which are formed. Both standard and competitive formats for homogeneous assays are also known in the art.

In a standard format, the amount of HCV antibodies forming the antibody-antigen complex is directly monitored. This may be accomplished by determining whether labeled anti-xenogenic (e.g., anti-human) antibodies which recognize an epitope on anti-HCV antibodies will bind due to complex formation. In a competitive format, the amount of HCV antibodies in the sample is deduced by monitoring the competitive effect on the binding of a known amount of labeled antibody (or other competing ligand) in the complex.

More particularly, complexes formed comprising anti-HCV antibody (or, in the case of competitive assays, the amount of competing antibody) are detected by any of a number of known techniques, depending on the format. For example, unlabeled HCV antibodies in the complex may be detected using a conjugate of antixenogeneic Ig complexed with a label, (e.g., an enzyme label). In an immunoprecipitation or agglutination assay format, the reaction between the HCV antigens and the antibody forms a network that precipitates from the solution or suspension and forms a visible layer or film of precipitate. If no anti-HCV antibody is present in the biological sample, no visible precipitate is formed. The above-described assay reagents, including the immunoassay solid support with bound antibodies and antigens, as well as antibodies and antigens to be reacted with the captured sample, can be provided in kits, with suitable instructions and other necessary reagents, in order to conduct immunoassays as described above. The kit will normally contain in separate containers the combination of antigens and/or antibodies (which may be bound to a solid support or separate with reagents for binding them to the solid support), control antibody and/or antigen formulations (positive and/or negative), labeled antibody and/or antigen when the assay format requires same and signal generating reagents (e.g., enzyme substrate) if the label does not generate a signal directly. Instructions (e.g., written, tape, VCR, CD-ROM, etc.) for carrying out the assay usually will be included in the kit. The kit can also contain, depending on the particular immunoassay used, other packaged reagents and materials (i.e. wash buffers and the like). Standard immunoassays, such as those described above, can be conducted using these kits.

Likewise, anti-HCV antibodies may also be used in virtually any assay format that employs a known antibody to detect antigens, in combination with known antigen to detect antibodies. As depicted in FIG. 7, the solid support is reacted with the HCV antigen (shown as NS4a/modified NS3 polypeptide) and also with anti-HCV core antibody.

III. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Cloning, expression, and purification of an NS4a/modified NS3 polypeptide conformational antigen to improve sensitivity of an immunoassay for early detection of Hepatitis C Virus-Specific antibodies.

Figure 3:
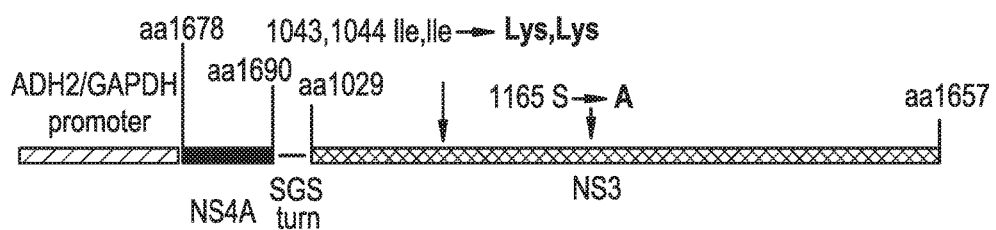
FIG. 3 is a diagrammatic representation of the turn mutant HCV expression cassette according to the subject invention.
Figure 4:
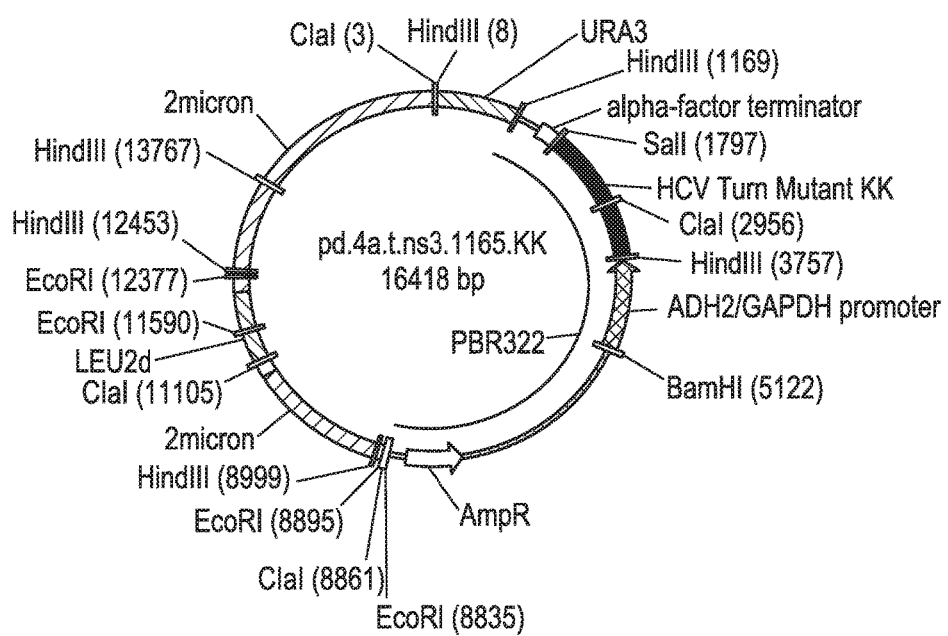
FIG. 4 is a circular map of the turn mutant expression plasmid pd.4a.t.ns3.1165.KK according to the subject invention.
Figure 5:
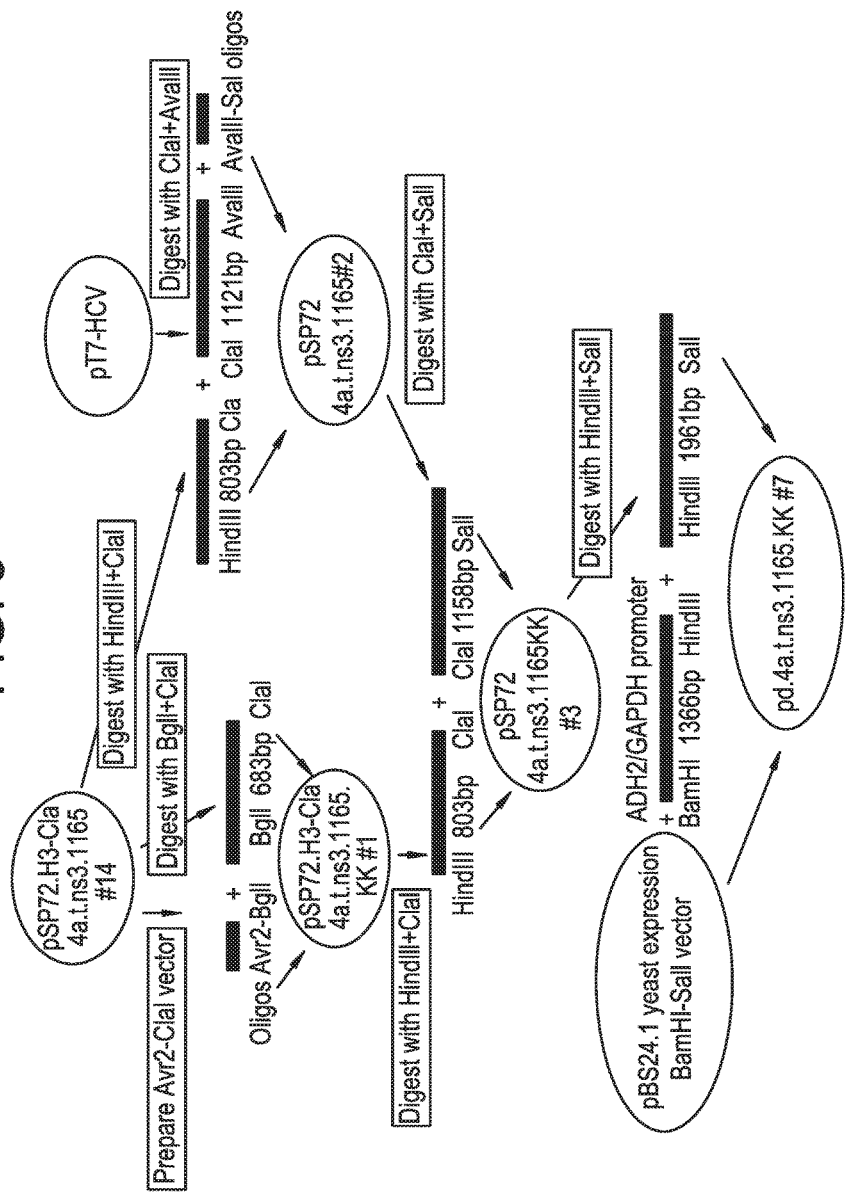
FIG. 5 illustrates the cloning procedure for the turn mutant expression plasmid pd.4a.t.ns3.1165.KK.

An HCV NS4a/NS3.KK mutant serine protease was genetically engineered for direct expression in *S. cerevisiae* (AD3 strain). The expression cassette was cloned into the pBS24.1 yeast expression vector (FIG. 2). The pBS24.1 yeast shuttle vector contains 2μ sequences for autonomous replication in yeast and the yeast genes leu2-d and URA-3 as selectable markers. The β-lactamase gene and the ColE1 origin of replication are required for plasmid replication in bacteria. The antigen/protein is expressed under the control of the hybrid ADH2/GAPDH promoter. The NS4a/NS3.KK mutant antigen (see FIG. 3) utilizes a 13aa segment of the NS4a protein (called minimal domain) attached to the N-terminus of the NS3 through a flexible SGS (Ser-Gly-Ser) sequence. This sequence allows the NS4a to fold into the pocket within the protease to create an enzymatically active molecule. To avoid self-hydrolysis due to the NS3 protease activity, Ser1165 (of SEQ ID NO:1) of the protease's catalytic triad was mutated to Ala, as previously described in U.S. Pat. No. 7,491,808B2. In addition, a pair of charged Lys residues were introduced on the N-terminus of the protease (HCV aa 1043 and 1044 of SEQ ID NO:1), replacing Ile residues, to improve the solubility of the purified NS4a/NS3 molecule. The NS3 domain described in U.S. Pat. No. 7,491,808B2 contains mutations at Tyr1428Pro and Ser1429Ile (with reference to SEQ ID NO:1)(abbreviated as the PI mutations, introduced to eliminate a protease cleavage site). These PI mutations are eliminated in the NS4a/NS3.KK mutant herein and returned to the native HCV1a sequence, Tyr1428 and Ser1429, since the activity of the serine protease has been eliminated. The Pro substitution at position 1428 of SEQ ID NO:1 may have had a destabilizing effect on the conformation of the NS4a/NS3 molecule.

FIG. 4 shows the circular map of the expression plasmid pd.4a.t.ns3.1165.KK (SEQ ID NO:2).

Cloning.

Plasmid pd.4a.t.ns3.1165.KK, encoding NS4a-turn-NS3 with three mutations (Ile1043Lys, Ile1044Lys, Ser1165Ala) was generated as follows in a four-step procedure.

First, the following DNA pieces were ligated together: (a) an Avr2-ClaI dephosphorylated vector prepared from pSP72.HindIII-Cla.4a.t.ns3.1165 #14, as described in U.S. Pat. No. 7,491,808. (The 803 bp HindIII-ClaI insert provides the sequence SEQ ID NO:5: ACAAAACAAA, the initiator ATG followed by codons for aa 1678 to 1690 of NS4, a Ser-Gly-Ser turn sequence and NS3 aa 1029 to 1274 (with reference to SEQ ID NO:1). Amino acid 1165 is mutated from Ser to Ala. pSP72 is a commercial vector from Promega, Madison, Wis., GenBank/EMBL Accession Number X65332); (b) synthetic oligonucleotides, AB-1 and AB-2, with Avr2-BglI restriction ends, encoding HCV aa 1040 to 1046 and introducing the desired Ile1043Lys and Ile1044Lys mutations; (c) a 683 bp BglI-ClaI DNA fragment gel-purified from pSP72.HindIII-Cla.4a.t.ns3.1165 #14; the BglI-ClaI fragment encodes HCV NS3 aa 1046 to 1274.

```
AB-1
SEQ ID NO: 6:
CTAGGGTGCAAGAAGACCAGCCTAAC

AB-2
SEQ ID NO: 7:
AGGCTGGTCTTCTTGCACC
```

The ligation mixture was transformed into HB101-competent cells and plated on Luria agar plates containing 100 ug/ml ampicillin. Miniprep analysis of individual clones led to the identification of putative positives which were amplified and sequenced. A clone with the correct sequence was named pSP72.HindIII-Cla.4a.t.ns3.1165.KK #1. An aliquot of the plasmid was subsequently transformed into *E. coli* strain SCS110 to avoid dam methylation which blocks a ClaI restriction site needed for a subsequent cloning step. (pT7HCV differs from the Choo et al. HCV SEQ ID NO:1 only in that amino acid residue 9 is R instead of K and amino acid residue 11 is T instead of N.)

Second, the following DNA pieces were ligated together for the purpose of cloning a ClaI-SalI fragment which would provide codons for NS3 aa 1274-1657 of native HCV1a sequence (SEQ ID NO:1): (a) a HindIII-SalI dephosphorylated vector prepared from pSP72; (b) an 803 bp HindIII-ClaI restriction fragment prepared from pSP72.HindIII-Cla.4a.t.ns3.1165 #14; (c) an 1121 bp ClaI-AvaIII restriction fragment, encoding NS3 aa 1274 to aa 1647, prepared from pT7HCV, a pUC18 construct containing the entire HCV1a genome (see SEQ ID NO:1), as described in U.S. Pat. No. 7,449,566 B2 (see also: Michael Vajdy et al., J of General Virology, 2006: 87, p. 2253-2262; (d) two AvaIII-SalI oligonucleotides, avsal-1 and avsal-2, which complete the NS3 sequence to aa 1657 and also encode two termination codons.

```
aysal-1
SEQ ID NO: 8:
TGTCGGCCGACCTGGAGGTCGTCACGTGATAAG aysal-2
SEQ ID NO: 9:
TCGACTTATCACGTGACGACCTCCAGGTCGGCCGACATGCA
```

The ligation mixture was transformed into HB101-competent cells and plated on Luria agar plates containing 100 ug/ml ampicillin. Miniprep analysis of individual clones led to the identification of putative positives which were amplified and sequenced. A clone with the correct sequence was named pSP72.4a.t.ns3.1165 #2. An aliquot of the plasmid was subsequently transformed into *E. coli* strain SCS110 to avoid dam methylation which blocks a ClaI restriction site.

Third, the following DNA pieces were ligated together for the purpose of cloning the entire 4a.t.ns3.1165.KK coding sequence into a subcloning vector, since attempts to clone it directly into the yeast expression vector were unsuccessful: (a) a HindIII-SalI dephosphorylated vector prepared from pSP72; (b) an 803 bp HindIII-ClaI fragment from pSP72.HindIII-Cla.4a t.ns3.1165.KK #1; (c) an 1158 bp ClaI-SalI fragment from pSP72.4a.t.ns3.1165 #2. The ligation mixture was transformed into HB101-competent cells and plated on Luria agar plates containing 100 ug/ml ampicillin. Miniprep analysis of individual clones led to the identification of a positive clone named pSP72.4a.t.ns3.1165.KK #3.

Finally, the following DNA pieces were ligated together to create the yeast expression plasmid: (a) a BamHI-SalI dephosphorylated pBS24.1 yeast expression vector; (b) a 1366 bp BamHI-HindIII fragment for the yeast hybrid promoter ADH2/GAPDH; (c) a 1961 bp HindIII-SalI fragment from pSP72.4a.t.ns3.1165.KK #3. The ligation mixture was transformed into HB101-competent cells. After miniscreen analysis, a clone with the expected BamHI-SalI restriction fragment of 3325 bp was identified as pd.4a.t.ns3.1165.KK #7 (FIG. 4).

Yeast Transformation.

*S. cerevisiae* strain AD3 (MATa, leu2, ura3-52, prb1-1122, pep4-3, prc1-407, ga12, [cir0], ::pDM15(pGAP/ADR1::G418R), ::Yip5ΔleuAD) was transformed with pd.4a.t.ns3.1165.KK #7 using the S.c.EasyComp Transformation Kit from Invitrogen, Carlsbad, Calif. Transformants grown on agar plates lacking uracil (Ura-agar plates with 8% glucose) were streaked for single colonies and patched onto Leu-8% glucose agar plates to increase the plasmid copy number. Leu-liquid starter cultures containing 7.1% glucose were grown for 24 hours at 30° C. and then diluted 1:20 into YEPD (1% yeast extract, 2% Bacto peptone, 2% glucose) medium. Cells were grown for 48 hours at 30° C. and at 25° C. To test for expression, aliquots of the cells were lysed with glass beads in lysis buffer. The recombinant protein was expressed at high levels in yeast, as detected by Coomassie blue staining and confirmed by immunoblot analysis using a monoclonal antibody anti-C33C 4D-1. (The antibody is described in Sansan Lin et. al, Journal of Clinical Microbiology, August 2005, p. 3917-3924.)

Purification of the recombinant HCV 4a.t.NS3.1165.KK protein ("TMKK" for turn mutant KK).

The TMKK protein (an NS4a/modified NS3 polypeptide) was purified as follows: S. cerevisiae cells expressing the NS4a.t.NS3.1165 KK turn mutant were harvested and suspended in lysis buffer (50 mM Tris-Cl pH 8.0, 10 mM EDTA, Roche Complete protease inhibitor tablets) and lysed in a Dyno-Mill (Wab Willy A. Bachofon, Basel, Switzerland) or equivalent apparatus using glass beads at a ratio of 1:1:1 cells:buffer:0.5 mm glass beads. After lysing for 35 minutes, a sample of the lysate was examined visually by microscopy to verify that cell breakage was at least 95% complete. The lysate was collected and centrifuged at 17,700 times g for 30 minutes at 4° C. and the pellet containing the insoluble protein was added to extraction buffer (50 mM Tris-Cl pH 8.0, 1 M NaCl, 10 mM EDTA; 2 ml/g of the initial cell pellet weight) and stirred in a beaker for 30 min at room temperature. The suspension was centrifuged at 30,100 times g for 30 minutes at 4° C., and the supernatant containing solubilized TMKK was collected for further purification.

Solid ammonium sulfate was added to the supernatant to a concentration of 30% and stirred on ice for three hours. The precipitate was collected by centrifugation at 30,100 times g for 30 minutes at 4° C. The pellet was resuspended in 1×PBS (0.5 ml/gm starting pellet weight), stirred for 30 minutes at room temperature, then diluted 4 fold with Dilution Buffer #1 (50 mM Tris-Cl pH 7.5, 50 mM NaCl, 5 mM DTT, 10% glycerol). The diluted suspension was gently stirred overnight at 4° C.

After overnight stirring, the suspension was centrifuged at 30,100 times g at 4° C. The supernatant was collected, diluted two-fold with Dilution Buffer #2 (50 mM IVIES pH 6.0, 5 mM DTT, 0.02% Tween-20, 10% glycerol) and applied to a SP Sepharose Fast Flow ion exchange column (GE Healthcare). Upon completion of loading, the column was washed with SP column buffer (50 mM MES pH 6.0, 37.5 mM NaCl, 5 mM DTT, 0.02% Tween-20, 10% glycerol), and TMKK was eluted from the column with an increasing NaCl gradient up to 0.7 M in column buffer. Fractions were pooled based on visual inspection of Coomassie stained SDS PAGE gels.

The pool containing SP Sepharose purified TMKK was diluted 2 fold with Dilution Buffer #3 (50 mM Tris-Cl pH 8.0, 5 mM DTT, 10% glycerol) and the pH was adjusted to 8.0. The sample was applied to a hydroxyapatite type II column (Bio-Rad) equilibrated in column buffer (50 mM Tris-Cl pH 8.0, 150 mM NaCl, 5 mM DTT, 0.02% Tween-20, 10% glycerol). Upon completion of loading, the column was washed with column buffer containing 200 mM NaCl. Fractions of the load and wash were collected until the absorbance measured at 280 nm returned to baseline. The column was stripped with a regeneration buffer (500 mM NaPO4 pH 7.0, 150 mM NaCl, 5 mM DTT, 0.02% Tween-20, 10% glycerol). The fractions were analyzed by SDS-PAGE, and the flowthrough and wash fractions containing purified TMKK protein were pooled. The pool was concentrated to 1 to 2 mg/ml using a 30 kD cutoff concentrator and then stored at −80° C.

Preparation of Reagents (1)

Abase buffer solution was prepared by adding disodium hydrogenphosphate for 1.627 g/L, potassium dihydrogenphosphate for 1.162 g/L, sodium chloride for 29.22 g/L, disodium edetate for 0.336 g/L, casein sodium for 1.0 g/L, and ProClin for 0.5 ml/L into a purified water, and adjusting the pH at approximately 7.3. A sample diluent was prepared by adding TWEEN20™ for 5 mL/L, SDS solution (1%) for 20 mL/L, yeast extract for 0.5 g/L, and BSA solution (30%) for 10 g/L into a suitable amount of the above base buffer solution, adjusting the pH at 6.4, and allowing the resulted solution to pass through a 0.22 μm membrane filter.

In the same manner, a marker buffer solution was prepared by adding sodium dihydrogenphosphate for 3.28 g/L, potassium phosphate for 13.28 g/L, sodium chloride for 17.56 g/L, disodium edetate for 0.372 g/L, Dextran T2000 for 10 g/L, sucrose 10 g/L, PVP (k=30) for 10 g/L, ProClin for 0.5 mL/L, BSA for 20 g/L, casein sodium for 3 g/L, inactivated horse serum for 20 mL/L, inactivated mouse serum for 10 mL/L, TRITON X-100™ for 10 mL/L, C14APS for 3 g/L, and C16TAB for 2 g/L into a purified water, adjusting the pH at approximately 7.2, and allowing the resulted solution to pass through the 0.22 μm membrane filter.

A substrate buffer solution was prepared by dissolving anhydrous citric acid for 4.936 g/L, and disodium hydrogenphosphate for 6.895 g/L in a purified water, adjusting the pH approximately at 4.9, and allowing the resulted solution to pass through the 0.22 μm membrane filter. A substrate reagent was prepared by dissolving o-phenylene diamine dihydrochloride of 13 mg tablet in the substrate buffer solution of 6 mL.

As a reaction stop reagent, 4N sulfuric acid was used.

A cleaning buffer solution was prepared by adding sodium dihydrogenphosphate for 1.09 g/L, potassium hydrogenphosphate for 0.31 g/L, sodium chloride for 8.2 g/L, Tween20 for 1 ml/L, and ProClin for 0.5 mL/L into a purified water, and allowing the resulted solution to pass through the 0.22 μm membrane filter.

A coating buffer solution for antigen solidification was prepared by adding sodium dihydrogenphosphate for 5.45 g/L, potassium hydrogenphosphate for 1.55 g, and disodium edetate for 0.744 g/L into a purified water. The coating buffer solution was added by HCV TMKK recombinant antigen or c200 recombinant antigen, each for 2.0 μg/mL.

A blocking buffer solution was prepared by adding phosphate buffer solution for a suitable amount, casein sodium for 10 g/L, and sucrose for 30 g/L into a purified water.

As a marker, a mouse antihuman IgG monoclonal antibody (2AHIGG2) purchased from the Institute of Immunology (Tokushu Meneki Kenkyusho) which was marked with HRP using a "(LK11) Peroxidase Labeling Kit NH2 (Dojin Kagaku Kenkyusho)" was used.

EXAMPLE 1

A coating buffer solution for antigen solidification that contains HCV TMKK recombinant antigen was dispensed in the amount of 200 μL/well, and statically left over one night at 4° C. After removing the liquid in the well, the well was washed for one time with a phosphate buffer solution. Then, a blocking buffer solution was dispensed in the amount of 300 μL/well, and statically left for more than four hours at room temperature. After removing the liquid in the well, the well was washed for one time with the cleaning buffer solution, and then dried to make a solid phase plate.

A sample diluent for 175 μL/well and each sample for 25 μL (commercially available human serum of U.S. ProMedDx) were dispensed in the solid phase plate, respectively, which were agitated by a plate mixer and incubated for one hour at 37° C. After removing the liquid in the well, the well was washed for five times with the cleaning buffer solution. Next, a liquid having a marker (i.e., an HRP marked mouse antihuman IgG monoclonal antibody) diluted for 5,000 folds with a marker dilute buffer solution was dispensed in the amount of 200 μL/well, which was incubated for 30 minutes at 37° C. After removing the liquid in the well, the well was washed for five times with the cleaning buffer solution. Then, a substrate liquid prepared by adding hydrogen peroxide (30%) in the amount of 0.1% in a substrate buffer solution was dispensed in the amount of 200 μL/well, and reacted for 30 minutes at room temperature. After dispensing a reaction stop solution in the amount of 50 μL/well, the absorbance was measured by means of two-wavelength measurement of 490 nm for the dominant wavelength and 650 nm for the sub wavelength using a plate reader (SpectraMax 340PC of Molecular Devices). The measured value is shown in Table 2.

COMPARATIVE EXAMPLE 1

A photometry is executed in the same procedure as Example 1 except for using a liquid containing c200 recombinant antigen instead of using the HCV TMKK recombinant antigen as a coating buffer solution for antigen solidification. The measured value is shown in Table 2.

COMPARATIVE EXAMPLE 2

RIBA3 (Ortho Diagnostic Systems) was used for detecting antibodies from the above samples according to the instruction manual. The result is shown in Table 2. In the table, the sample number in parentheses is the sample number assigned by ProMedDx. The "NHS" is a normal human serum and was used as a negative control.

As shown in Table 2, detection or quantification of hepatitis C virus using TMKK in Example 1 showed higher sensitivity than using c200 in Comparative Example 1. Specifically, detection of hepatitis C virus antibody was confirmed with the samples 4 to 23 in Comparative Example 2. However, the quantification using c200 in Comparative Example 1 showed unreasonably low sensitivity, especially for samples 4, 5, and 14, while the quantification using TMKK in Example 1 showed high detection sensitivity. The samples in which hepatitis C virus antibody is not present such as the samples 1 to 3 exhibited lower quantification value even in Example 1. There is no problem in the accuracy of detection or quantification. Note that the c33c positive result of RIBA for sample 10 was likely due to cross reaction.

EXAMPLE 2

A photometry was executed in the same procedure as Example 1 except for using samples in panels "6212", "6215", and "9058" of seroconversion panel (ZeptoMetrix) in which hepatitis C virus infection is confirmed through genetic screening. The measured values are shown in Tables 3 to 5. As the branch number of the samples (e.g., "-1", "-2") increases, it signifies the later blood collecting date of the sample, i.e., signifying more progressed hepatitis C virus infection. Known results of RIBA3 measurement for each sample are also shown in Tables 3 to 5.

COMPARATIVE EXAMPLE 2

A photometry was executed in the same procedure as Comparative Example 1 except for using samples in panels "6212", "6215", and "9058" of seroconversion panel (ZeptoMetrix). The measured values are shown in Tables 3 to 5.

For the samples at an early stage of infection as in the panels 6212-02 and 6212-03 shown in Table 3, the detection of antibodies was successful using TMKK in Example 2, but failed using c200 in Comparative Example 2 and with the RIBA3. In addition, the detection of antibodies on the panels 6212-04 and 6212-05 was successful using TMKK in Example 2 and c200 in Comparative Example 2, however, the detection sensitivity was higher using TMKK in Example 2.

As shown in Table 4, the detection of antibodies on the panel 6215-04 was successful using TMKK in Example 2, however, failed using c200 in Comparative Example 2. Since the sensitivity of the reagent of the present invention was equal to or more than the core antigen (C22) known for having a relatively high detection sensitivity, it was confirmed that a combined use with a core antigen is not always necessary if the reagent of the present invention is used.

As shown in Table 5, the detection of antibodies on a sample of early stage of infection such as the panel 9058-04 was successful using TMKK in Example 2 and with the RIBA3, but failed using c200 in Comparative Example 2. The sample is a core antibody seroconverter as indicated by the RIBA3 result, suggesting the suitability of combined use with the core antigen (C22) known for having relatively high detection sensitivity. In addition, the detection of antibodies on the panels 9058-05 was successful using both TMKK in Example 2 and using c200 in Comparative Example 2. However, the sensitivity was higher using TMKK in Example 2.

Preparation of Reagents (2)

The reagents prepared in the above mentioned "Preparation of reagents (1)" are used except for the reagents described below.

A sample diluent was prepared by adding TWEEN20™ for 5 mL/L, SDS solution (1%) for 20 mL/L, yeast extract for 0.5 g/L, BSA solution (30%) for 10 g/L, LDAO for 5 g/L, and DTT 1 mM into the proper amount of base buffer solution described above, adjusting the pH at 7.3, and allowing the resulted solution to pass through a 0.22 μm membrane filter.

A coating buffer solution for antibody solidification was prepared by adding sodium chloride for 5.85 g/L, acetic anhydride sodium for 5.18 g/L, acetic acid for 2.2 mL/L, and ammonium sulfates for 114 g/L into a purified water, and adjusting the pH approximately at 4.8. The coating solution was added by c11-3 monoclonal antibody and c11-7 monoclonal antibody for 1.8 μg/mL respectively.

As a marker, a labeled antibody included in "HCV core Ag ELISA Kit (Ortho Diagnostic Systems) was used for the antigen detection, while an HCV TMKK recombinant antigen which was marked with HRP by using "(LK11) Peroxidase Labeling Kit NH2 (Dojin Kagaku Kenkyusho) was used for the antibody detection.

EXAMPLE 3

The above coating buffer solution for antibody solidification was dispensed in the amount of 200 μL/well into a 96 well microplate (Corning high-bind type), and statically left for six hours at room temperature. After removing the liquid in the well, the well was washed for three times with a phosphate buffer solution. Next, above coating buffer solution for antigen solidification was dispensed in the amount of 200 μL/well, and left for one night at 4° C. After removing the liquid in the well, the well was washed for one time with the phosphate buffer solution. Then, a blocking buffer solution was dispensed in the amount of 300 μL/well, and statically left for more than four hours at room temperature. After removing the liquid in the well, the well was washed for one time with the cleaning buffer solution, and then dried to make a solid phase plate.

A sample diluent in the amount of 150 μL/well, and "6212" and "6224" of seroconversion panel (ZeproMetrix) as a sample in the amount of 50 μL were dispensed into the solid phase plate, respectively, which were agitated by a plate mixer, and incubated for one hour at 37° C. After removing the liquid in the well, the well was washed for five times with the cleaning buffer solution. Next, a liquid in which a marker (i.e., an HRP marked HCV TMKK recombinant antigen) diluted for 40,000 folds by a marker dilute buffer solution, and a liquid in which a marker (i.e., an HRP marked anti-HCV core antibody) diluted for 100 folds by a marker diluted buffer solution were dispensed in the amount of 200 μL/well, which was incubated for 30 minutes at 37° C. After removing the liquid in the well, the well was washed for five times with the cleaning buffer solution. Then, a substrate liquid prepared by adding hydrogen peroxide (30%) in the amount of 0.1% in a substrate buffer solution was dispensed in the amount of 200 μL/well and reacted for 30 minutes at room temperature. After dispensing a reaction stop solution in the amount of 50 μL/well, a photometry was executed by measuring the absorbance through two-wavelength measurement of 490 nm for the dominant wavelength and 650 nm for the sub wavelength using a plate reader (SpectraMax 340PC of Molecular Devices). The results are shown in Tables 6 and 7. Known results of RIBA3 measurement for each sample are also shown in Tables 6 and 7. The COI in the table is a value calculated by measuring 10 units of HCV antibody negative samples with applying a cutoff value in which the OD average value is added by 10SD.

As the Comparative Example 3, a photometry was executed in the same procedure as Example 3 except for: using "Monolisa HCV Ag-Ab (Bio-Rad)", a commercially available HCV antigen-antibody detection kit instead of the quantification reagent of the present invention; conducting a test according to the instruction manual of the kit; and determining the OD and COI. As the Comparative Example 4, known COI of "HCV Ag/Ab Combo (ABBOTT)" for each sample is shown in Tables 6 and 7. Moreover, as the Comparative Example 5, the results of antibody amount measurement in each sample using "LUMTPULSE™ Ortho HCV antigen (Ortho Diagnostic Systems) according to the instruction manual is shown in Tables 6 and 7. Known results of RIBA3 measurement for each sample are also shown in Tables 6 and 7.

As shown in Table 6, for samples at an early stage of infection such as panels 6212-01 and 6212-02, the detection of HCV was successful using anti HCV core Abs and TMKK in Example 3, failed in Comparative Example 4, and was successful but with low sensitivity in Comparative Example 4 compared to Comparative Example 3. In addition, as shown in the panels 6212-05 and 6212-06, the HCV detection in samples at the stage of decreasing antigen amount failed in Comparative Example 5, however, the HCV detection was possible using anti HCV core Abs and TMKK in Example 3.

As shown in Table 7, for samples at an early stage of infection such as panels 6224-01 to 6224-03, the detection of HCV was successful using anti HCV core Abs and TMKK in Example 3 with higher sensitivity than in Comparative Example 3. In addition, as shown in the panel 6224-04, the HCV detection in samples at the stage of decreasing antigen amount failed in Comparative Example 4, however, it was successful using anti HCV core Abs and TMKK in Example 3.

While particular embodiments of the invention have been shown, it will be understood, of course, that the invention is not limited thereto, since modifications may be made by those skilled in the art, particularly in light of the foregoing teachings. Reasonable variation and modification are possible within the scope of the foregoing disclosure of the invention without departing from the spirit of the invention.

TABLE 1

| Domain | Approximate Boundaries* |
|---|---|
| C (core) | 1-191 of SEQ ID NO: 1 |
| E1 | 192-383 of SEQ ID NO: 1 |
| E2 | 384-746 of SEQ ID NO: 1 |
| P7 | 747-809 of SEQ ID NO: 1 |
| NS2 | 810-1026 of SEQ ID NO: 1 |
| NS3 | 1027-1657 of SEQ ID NO: 1 |
| NS4a | 1658-1711 of SEQ ID NO: 1 |
| NS4b | 1712-1972 of SEQ ID NO: 1 |
| NS5a | 1973-2420 of SEQ ID NO: 1 |
| NS5b | 2421-3011 of SEQ ID NO: 1 |

*Numbered relative to HCV-1. See, Choo et al. (1991) Proc. Natl. Acad. Sci. USA 88: 2451-2455.

TABLE 2

| | TMKK c200 | | | | | | |
|---|---|---|---|---|---|---|---|
| Sample | Comparative Example 2 (RIBA3) | | | | | | Comparative |
| number | c100p | c33c | c22p | NS5 | SOD | Example 1 | Example 1 |
| 1(NHS) | | | | | | 0.017 | 0.020 |
| 2(007) | − | − | − | ± | − | 0.015 | 0.017 |
| 3(011) | − | ± | − | − | − | 0.066 | 0.019 |
| 4(053) | − | − | 2+ | − | − | 0.785 | 0.060 |
| 5(077) | ± | ± | 3+ | − | − | 0.760 | 0.020 |
| 6(057) | ± | ± | 3+ | − | − | 2.049 | 0.175 |
| 7(037) | ± | ± | 4+ | − | − | 2.220 | 0.357 |
| 8(059) | 1+ | ± | 4+ | − | − | 3.254 | 3.090 |
| 9(034) | − | ± | 4+ | 3+ | − | 3.200 | 0.515 |
| 10(006) | − | 3+ | − | ± | − | 0.042 | 0.145 |
| 11(093) | 2+ | 1+ | ± | − | − | 2.007 | 0.324 |
| 12(026) | ± | 1+ | ± | 1+ | − | 1.785 | 0.129 |
| 13(048) | − | 1+ | 1+ | − | − | 2.495 | 0.295 |
| 14(064) | ± | 1+ | 4+ | 1+ | − | 1.574 | 0.093 |
| 15(088) | − | 3+ | 1+ | − | − | 2.183 | 0.830 |
| 16(004) | 1+ | 3+ | 4+ | − | − | 3.953 | 3.156 |
| 17(076) | ± | 4+ | − | − | − | 0.961 | 0.495 |
| 18(012) | − | 4+ | − | 4+ | − | 3.562 | 3.569 |
| 19(025) | ± | 4+ | − | 4+ | − | 2.640 | 2.586 |
| 20(033) | 2+ | 4+ | − | 4+ | − | 3.332 | 1.939 |
| 21(031) | 4+ | 4+ | ± | ± | − | 3.048 | 2.586 |
| 22(094) | 4+ | 4+ | 4+ | − | − | 3.954 | 3.956 |
| 23(002) | 4+ | 4+ | 4+ | 4+ | − | 3.550 | 3.356 |

TABLE 3

| | | TMKK c200 | | | | | | |
|---|---|---|---|---|---|---|---|---|
| Panel number | Blood collecting day | Example 2 OD | Comparative Example 2 OD | RIBA3.0 | | | | |
| | | | | C100 | C33 | C22 | NS5 | SOD |
| 6212-01 | Nov. 16, 1995 | 0.004 | 0.006 | − | − | − | − | − |
| 6212-02 | Nov. 28, 1995 | 0.237 | 0.026 | − | +/− | − | − | − |
| 6212-03 | Nov. 30, 1995 | 0.270 | 0.034 | − | +/− | − | − | − |
| 6212-04 | Dec. 9, 1995 | 0.416 | 0.238 | − | 1+ | − | − | − |
| 6212-05 | Dec. 12, 1995 | 0.828 | 0.476 | − | 1+ | − | − | − |
| 6212-06 | Dec. 18, 1995 | 1.111 | 0.688 | − | 1+ | − | − | − |
| 6212-07 | Dec. 23, 1995 | 1.158 | 1.081 | − | 1+ | − | − | − |
| 6212-08 | Jan. 8, 1996 | 3.615 | 3.946 | − | 4+ | − | − | − |
| 6212-09 | Jan. 10, 1996 | 3.946 | 3.936 | − | 4+ | − | − | − |

TABLE 4

| | | TMKK c200 | | | | | | |
|---|---|---|---|---|---|---|---|---|
| Panel number | Blood collecting day | Example 2 OD | Comparative Example 2 OD | RIBA3.0 | | | | |
| | | | | C100 | C33 | C22 | NS5 | SOD |
| 6215-01 | Jan. 19, 1996 | 0.006 | 0.015 | − | − | − | − | − |
| 6215-02 | Jan. 22, 1996 | 0.007 | 0.014 | − | − | − | − | − |
| 6215-03 | Jan. 29, 1996 | 0.008 | 0.016 | − | − | − | − | − |
| 6215-04 | Feb. 8, 1996 | 0.131 | 0.038 | − | +/− | 4+ | − | − |

TABLE 5

| | | TMKK c200 | | | | | | |
|---|---|---|---|---|---|---|---|---|
| Panel number | Blood collecting day | Example 2 OD | Comparative Example 2 OD | RIBA3.0 | | | | |
| | | | | C100 | C33 | C22 | NS5 | SOD |
| 9058-01 | Mar. 6, 1998 | 0.026 | 0.014 | − | − | +/− | − | − |
| 9058-02 | Mar. 9, 1998 | 0.029 | 0.013 | − | − | +/− | − | − |
| 9058-03 | Mar. 13, 1998 | 0.058 | 0.015 | − | +/− | + | − | − |
| 9058-04 | Mar. 16, 1998 | 0.142 | 0.027 | − | 1+ | 1+ | − | − |
| 9058-05 | Mar. 20, 1998 | 0.228 | 0.081 | − | 1+ | 2+ | − | − |

TABLE 6

| | combo: anti HCV core Abs + TMKK | | | | | | | | | | |
|---|---|---|---|---|---|---|---|---|---|---|---|
| | Example 3 | | Comparative Example 3 Bio-Rad Monolisa HCV Ag-Ab | | Comparative Example 4 ABBOTT HCV Ag/Ab Combo | Comparative Example 5 Lumi HCV Ag | RIBA 3.0 | | | | |
| | OD | COI | OD | COI | COI | fmol/l | c100p | c33c | c22p | NS5 | SOD |
| 6212-01 | 0.127 | 2.3 | 0.107 | 0.38 | 0.81 | 2198.5 | − | − | − | − | − |
| 6212-02 | 0.704 | 12.9 | 0.218 | 0.78 | 0.53 | 166.5 | − | +/− | − | − | − |
| 6212-03 | 0.849 | 15.5 | 0.290 | 1.03 | 0.61 | 108.5 | − | +/− | − | − | − |
| 6212-04 | 1.687 | 30.8 | 1.065 | 3.79 | 0.66 | 129.5 | − | 1+ | − | − | − |
| 6212-05 | 1.591 | 29.1 | 1.360 | 4.85 | 0.63 | 0.5 | − | 1+ | − | − | − |
| 6212-06 | 1.616 | 29.5 | 1.478 | 5.27 | 0.59 | 27.5 | − | 1+ | − | − | − |
| 6212-07 | 1.453 | 26.6 | 1.490 | 5.31 | 0.64 | 271.0 | − | 1+ | − | − | − |
| 6212-08 | 2.207 | 40.3 | 2.096 | 7.47 | 2.25 | 276.0 | − | 4+ | − | − | − |
| 6212-09 | 1.980 | 36.2 | 2.140 | 7.63 | 2.44 | 401.0 | − | 4+ | − | − | − |

TABLE 7

| | combo: anti HCV core Abs + TMKK | | | | | | | | | |
|---|---|---|---|---|---|---|---|---|---|---|
| | Example 3 | | Comparative Example 3 Bio-Rad Monolisa HCV Ag-Ab | | Comparative Example 4 ABBOTT HCV Ag/Ab Combo | Comparative Example 5 Lumi HCV Ag | RIBA 3.0 | | | | |
| | OD | COI | OD | COI | COI | fmol/l | c100p | c33c | c22p | NS5 | SOD |
| 6224-01 | 0.209 | 2.4 | 0.077 | 0.27 | 1.565 | 1951.6 | − | − | − | − | − |
| 6224-02 | 0.140 | 1.6 | 0.091 | 0.32 | 1.732 | 2361.2 | − | − | − | − | − |
| 6224-03 | 0.287 | 3.3 | 0.097 | 0.34 | 1.388 | 2184.0 | − | − | − | − | − |
| 6224-04 | 0.153 | 1.7 | 0.072 | 0.26 | 0.866 | 943.8 | − | +/− | − | − | − |
| 6224-05 | 0.469 | 5.3 | 0.536 | 1.90 | 4.137 | 2175.4 | − | 1 | − | − | − |
| 6224-06 | 0.558 | 6.4 | 0.818 | 2.91 | 4.599 | 1959.2 | − | 2 | − | − | − |

The invention claimed is:

1. An immunoassay reagent comprising a polypeptide, the polypeptide comprising: a hepatitis C virus NS4a domain having SEQ ID NO:3; a modified hepatitis C virus NS3 domain having SEQ ID NO:4, wherein one or more amino acid residues of SEQ ID NO:4 are modified such that protease activity of the modified hepatitis C virus NS3 domain is inhibited relative to protease activity of the hepatitis C virus NS3 domain having SEQ ID NO:4 lacking the modification; and an intervening region connecting the carboxy terminus of the NS4a domain to the amino terminus of the modified NS3 domain; wherein the one or more amino acid residues of SEQ ID NO:4 comprises one or more of amino acid residues 55, 79, and 137 of SEQ ID NO:4.

2. The immunoassay reagent of claim 1, wherein the modification comprises a substitution of alanine or glycine.

3. The immunoassay reagent of claim 2, wherein the modification comprises a substitution of alanine for amino acid residue 137.

4. The immunoassay reagent of claim 1, wherein the intervening region of the polypeptide has the amino acid sequence SGS.

5. The immunoassay reagent of claim 1, wherein the polypeptide has the amino acid sequence as shown in SEQ ID NO:2.

6. The immunoassay reagent of claim 1 bound to a solid support.

7. A method of detecting antibodies to hepatitis C virus in a biological sample, said method comprising: (a) providing the immunoassay reagent of claim 1; (b) combining a biological sample with said immunoassay reagent under conditions which allow HCV antibodies, when present in the biological sample, to bind to said immunoassay reagent to form a first immune complex;
(c) adding to the first immune complex from step (b) a labeled detector, wherein said labeled detector is reactive with said first immune complex; and (d) detecting second immune complexes formed between the labeled detector and the first immune complex, if any, as an indication of the presence of antibodies to hepatitis C virus in the biological sample.

8. The method of claim 7 wherein the labeled detector is a labeled antibody or labeled antigen.

9. The method of claim 7 wherein the immunoassay reagent is bound to a solid support.

10. A method of detecting antibodies to hepatitis C virus and/or hepatitis C virus antigen in a biological sample, said method comprising: (a) providing the immunoassay reagent of claim 1; (b) combining a biological sample with said immunoassay reagent and one or more anti-HCV antibodies under conditions which allow HCV antibodies, when present in the biological sample, to bind to said immunoassay reagent to form a first immune complex, and which further allows HCV antigens, when present in the biological sample, to bind to said anti-HCV antibodies to form a second immune complex; (c) adding to the first immune complex from step (b) a first labeled detector, wherein said first labeled detector is reactive with said first immune complex, and adding to the second immune complex from step (b) a second labeled detector, wherein said second labeled detector is reactive with the second immune complex; and (d) detecting third immune complexes formed between the first labeled detector and the first immune complex, if any, and detecting fourth immune complexes formed between the second labeled detector and the second immune complex, if any, as an indication of the presence of antibodies to HCV and/or HCV antigen in the biological sample.

11. The method of claim 10 wherein the first labeled detector and the second labeled detector are each labeled antibody or labeled antigen.

12. The method of claim 10 wherein one or more of the immunoassay reagent and the one or more anti-HCV antibodies are bound to the same or different solid supports.

13. An immunodiagnostic test kit comprising the immunoassay reagent of claim 1, and instructions for conducting the immunodiagnostic test.

14. The immunodiagnostic test kit of claim 13, further comprising one or more anti-HCV antibodies.

15. The immunodiagnostic test kit of claim 14, wherein the one or more anti-HCV antibodies are an anti-HCV core antibodies.

16. An isolated polypeptide comprising the amino acid sequence SEQ ID NO:2.

17. An isolated polypeptide consisting of the amino acid sequence SEQ ID NO:2.

* * * * *

SEQUENCE LISTING

<160> NUMBER OF SEQ ID NOS: 9

<210> SEQ ID NO 1
<211> LENGTH: 1860
<212> TYPE: PRT
<213> ORGANISM: Hepatitis C virus

<400> SEQUENCE: 1

```
Met Ser Thr Asn Pro Lys Pro Gln Lys Lys Asn Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
            180                 185                 190

Gln Val Arg Asn Ser Thr Gly Leu Tyr His Val Thr Asn Asp Cys Pro
        195                 200                 205

Asn Ser Ser Ile Val Tyr Glu Ala Ala Asp Ala Ile Leu His Thr Pro
    210                 215                 220

Gly Cys Val Pro Cys Val Arg Glu Gly Asn Ala Ser Arg Cys Trp Val
225                 230                 235                 240

Ala Met Thr Pro Thr Val Ala Thr Arg Asp Gly Lys Leu Pro Ala Thr
                245                 250                 255
```

-continued

```
Gln Leu Arg Arg His Ile Asp Leu Leu Val Gly Ser Ala Thr Leu Cys
            260                 265                 270

Ser Ala Leu Tyr Val Gly Asp Leu Cys Gly Ser Val Phe Leu Val Gly
        275                 280                 285

Gln Leu Phe Thr Phe Ser Pro Arg Arg His Trp Thr Thr Gln Gly Cys
    290                 295                 300

Asn Cys Ser Ile Tyr Pro Gly His Ile Thr Gly His Arg Met Ala Trp
305                 310                 315                 320

Asp Met Met Met Asn Trp Ser Pro Thr Thr Ala Leu Val Met Ala Gln
                325                 330                 335

Leu Leu Arg Ile Pro Gln Ala Ile Leu Asp Met Ile Ala Gly Ala His
            340                 345                 350

Trp Gly Val Leu Ala Gly Ile Ala Tyr Phe Ser Met Val Gly Asn Trp
        355                 360                 365

Ala Lys Val Leu Val Val Leu Leu Phe Ala Gly Val Asp Ala Glu
    370                 375                 380

Thr His Val Thr Gly Gly Ser Ala Gly His Thr Val Ser Gly Phe Val
385                 390                 395                 400

Ser Leu Leu Ala Pro Gly Ala Lys Gln Asn Val Gln Leu Ile Asn Thr
                405                 410                 415

Asn Gly Ser Trp His Leu Asn Ser Thr Ala Leu Asn Cys Asn Asp Ser
            420                 425                 430

Leu Asn Thr Gly Trp Leu Ala Gly Leu Phe Tyr His His Lys Phe Asn
        435                 440                 445

Ser Ser Gly Cys Pro Glu Arg Leu Ala Ser Cys Arg Pro Leu Thr Asp
    450                 455                 460

Phe Asp Gln Gly Trp Gly Pro Ile Ser Tyr Ala Asn Gly Ser Gly Pro
465                 470                 475                 480

Asp Gln Arg Pro Tyr Cys Trp His Tyr Pro Lys Pro Cys Gly Ile
                485                 490                 495

Val Pro Ala Lys Ser Val Cys Gly Pro Val Tyr Cys Phe Thr Pro Ser
            500                 505                 510

Pro Val Val Val Gly Thr Thr Asp Arg Ser Gly Ala Pro Thr Tyr Ser
        515                 520                 525

Trp Gly Glu Asn Asp Thr Asp Val Phe Val Leu Asn Asn Thr Arg Pro
    530                 535                 540

Pro Leu Gly Asn Trp Phe Gly Cys Thr Trp Met Asn Ser Thr Gly Phe
545                 550                 555                 560

Thr Lys Val Cys Gly Ala Pro Pro Cys Val Ile Gly Gly Ala Gly Asn
                565                 570                 575

Asn Thr Leu His Cys Pro Thr Asp Cys Phe Arg Lys His Pro Asp Ala
            580                 585                 590

Thr Tyr Ser Arg Cys Gly Ser Gly Pro Trp Ile Thr Pro Arg Cys Leu
        595                 600                 605

Val Asp Tyr Pro Tyr Arg Leu Trp His Tyr Pro Cys Thr Ile Asn Tyr
    610                 615                 620

Thr Ile Phe Lys Ile Arg Met Tyr Val Gly Gly Val Glu His Arg Leu
625                 630                 635                 640

Glu Ala Ala Cys Asn Trp Thr Arg Gly Glu Arg Cys Asp Leu Glu Asp
                645                 650                 655

Arg Asp Arg Ser Glu Leu Ser Pro Leu Leu Leu Thr Thr Thr Gln Trp
            660                 665                 670
```

-continued

```
Gln Val Leu Pro Cys Ser Phe Thr Thr Leu Pro Ala Leu Ser Thr Gly
            675                 680                 685

Leu Ile His Leu His Gln Asn Ile Val Asp Val Gln Tyr Leu Tyr Gly
        690                 695                 700

Val Gly Ser Ser Ile Ala Ser Trp Ala Ile Lys Trp Glu Tyr Val Val
705                 710                 715                 720

Leu Leu Phe Leu Leu Leu Ala Asp Ala Arg Val Cys Ser Cys Leu Trp
                725                 730                 735

Met Met Leu Leu Ile Ser Gln Ala Glu Ala Ala Leu Glu Asn Leu Val
            740                 745                 750

Ile Leu Asn Ala Ala Ser Leu Ala Gly Thr His Gly Leu Val Ser Phe
        755                 760                 765

Leu Val Phe Phe Cys Phe Ala Trp Tyr Leu Lys Gly Lys Trp Val Pro
    770                 775                 780

Gly Ala Val Tyr Thr Phe Tyr Gly Met Trp Pro Leu Leu Leu Leu Leu
785                 790                 795                 800

Leu Ala Leu Pro Gln Arg Ala Tyr Ala Leu Asp Thr Glu Val Ala Ala
                805                 810                 815

Ser Cys Gly Gly Val Leu Val Gly Leu Met Ala Leu Thr Leu Ser
            820                 825                 830

Pro Tyr Tyr Lys Arg Tyr Ile Ser Trp Cys Leu Trp Trp Leu Gln Tyr
        835                 840                 845

Phe Leu Thr Arg Val Glu Ala Gln Leu His Val Trp Ile Pro Pro Leu
    850                 855                 860

Asn Val Arg Gly Gly Arg Asp Ala Val Ile Leu Leu Met Cys Ala Val
865                 870                 875                 880

His Pro Thr Leu Val Phe Asp Ile Thr Lys Leu Leu Leu Ala Val Phe
                885                 890                 895

Gly Pro Leu Trp Ile Leu Gln Ala Ser Leu Leu Lys Val Pro Tyr Phe
        900                 905                 910

Val Arg Val Gln Gly Leu Leu Arg Phe Cys Ala Leu Ala Arg Lys Met
    915                 920                 925

Ile Gly Gly His Tyr Val Gln Met Val Ile Ile Lys Leu Gly Ala Leu
930                 935                 940

Thr Gly Thr Tyr Val Tyr Asn His Leu Thr Pro Leu Arg Asp Trp Ala
945                 950                 955                 960

His Asn Gly Leu Arg Asp Leu Ala Val Ala Val Glu Pro Val Val Phe
                965                 970                 975

Ser Gln Met Glu Thr Lys Leu Ile Thr Trp Gly Ala Asp Thr Ala Ala
            980                 985                 990

Cys Gly Asp Ile Ile Asn Gly Leu Pro Val Ser Ala Arg Arg Gly Arg
        995                 1000                1005

Glu Ile Leu Leu Gly Pro Ala Asp Gly Met Val Ser Lys Gly Trp
    1010                1015                1020

Arg Leu Leu Ala Pro Ile Thr Ala Tyr Ala Gln Gln Thr Arg Gly
    1025                1030                1035

Leu Leu Gly Cys Ile Ile Thr Ser Leu Thr Gly Arg Asp Lys Asn
    1040                1045                1050

Gln Val Glu Gly Glu Val Gln Ile Val Ser Thr Ala Ala Gln Thr
    1055                1060                1065

Phe Leu Ala Thr Cys Ile Asn Gly Val Cys Trp Thr Val Tyr His
    1070                1075                1080

Gly Ala Gly Thr Arg Thr Ile Ala Ser Pro Lys Gly Pro Val Ile
```

```
              1085                1090                1095
Gln Met Tyr Thr Asn Val Asp Gln Asp Leu Val Gly Trp Pro Ala
        1100                1105                1110
Pro Gln Gly Ser Arg Ser Leu Thr Pro Cys Thr Cys Gly Ser Ser
        1115                1120                1125
Asp Leu Tyr Leu Val Thr Arg His Ala Asp Val Ile Pro Val Arg
        1130                1135                1140
Arg Arg Gly Asp Ser Arg Gly Ser Leu Leu Ser Pro Arg Pro Ile
        1145                1150                1155
Ser Tyr Leu Lys Gly Ser Ser Gly Gly Pro Leu Leu Cys Pro Ala
        1160                1165                1170
Gly His Ala Val Gly Ile Phe Arg Ala Ala Val Cys Thr Arg Gly
        1175                1180                1185
Val Ala Lys Ala Val Asp Phe Ile Pro Val Glu Asn Leu Glu Thr
        1190                1195                1200
Thr Met Arg Ser Pro Val Phe Thr Asp Asn Ser Ser Pro Pro Val
        1205                1210                1215
Val Pro Gln Ser Phe Gln Val Ala His Leu His Ala Pro Thr Gly
        1220                1225                1230
Ser Gly Lys Ser Thr Lys Val Pro Ala Ala Tyr Ala Ala Gln Gly
        1235                1240                1245
Tyr Lys Val Leu Val Leu Asn Pro Ser Val Ala Ala Thr Leu Gly
        1250                1255                1260
Phe Gly Ala Tyr Met Ser Lys Ala His Gly Ile Asp Pro Asn Ile
        1265                1270                1275
Arg Thr Gly Val Arg Thr Ile Thr Thr Gly Ser Pro Ile Thr Tyr
        1280                1285                1290
Ser Thr Tyr Gly Lys Phe Leu Ala Asp Gly Gly Cys Ser Gly Gly
        1295                1300                1305
Ala Tyr Asp Ile Ile Ile Cys Asp Glu Cys His Ser Thr Asp Ala
        1310                1315                1320
Thr Ser Ile Leu Gly Ile Gly Thr Val Leu Asp Gln Ala Glu Thr
        1325                1330                1335
Ala Gly Ala Arg Leu Val Val Leu Ala Thr Ala Thr Pro Pro Gly
        1340                1345                1350
Ser Val Thr Val Pro His Pro Asn Ile Glu Glu Val Ala Leu Ser
        1355                1360                1365
Thr Thr Gly Glu Ile Pro Phe Tyr Gly Lys Ala Ile Pro Leu Glu
        1370                1375                1380
Val Ile Lys Gly Gly Arg His Leu Ile Phe Cys His Ser Lys Lys
        1385                1390                1395
Lys Cys Asp Glu Leu Ala Ala Lys Leu Val Ala Leu Gly Ile Asn
        1400                1405                1410
Ala Val Ala Tyr Tyr Arg Gly Leu Asp Val Ser Val Ile Pro Thr
        1415                1420                1425
Ser Gly Asp Val Val Val Ala Thr Asp Ala Leu Met Thr Gly
        1430                1435                1440
Tyr Thr Gly Asp Phe Asp Ser Val Ile Asp Cys Asn Thr Cys Val
        1445                1450                1455
Thr Gln Thr Val Asp Phe Ser Leu Asp Pro Thr Phe Thr Ile Glu
        1460                1465                1470
Thr Ile Thr Leu Pro Gln Asp Ala Val Ser Arg Thr Gln Arg Arg
        1475                1480                1485
```

Gly Arg Thr Gly Arg Gly Lys Pro Gly Ile Tyr Arg Phe Val Ala
1490                1495                1500

Pro Gly Glu Arg Pro Ser Gly Met Phe Asp Ser Ser Val Leu Cys
1505                1510                1515

Glu Cys Tyr Asp Ala Gly Cys Ala Trp Tyr Glu Leu Thr Pro Ala
1520                1525                1530

Glu Thr Thr Val Arg Leu Arg Ala Tyr Met Asn Thr Pro Gly Leu
1535                1540                1545

Pro Val Cys Gln Asp His Leu Glu Phe Trp Glu Gly Val Phe Thr
1550                1555                1560

Gly Leu Thr His Ile Asp Ala His Phe Leu Ser Gln Thr Lys Gln
1565                1570                1575

Ser Gly Glu Asn Leu Pro Tyr Leu Val Ala Tyr Gln Ala Thr Val
1580                1585                1590

Cys Ala Arg Ala Gln Ala Pro Pro Pro Ser Trp Asp Gln Met Trp
1595                1600                1605

Lys Cys Leu Ile Arg Leu Lys Pro Thr Leu His Gly Pro Thr Pro
1610                1615                1620

Leu Leu Tyr Arg Leu Gly Ala Val Gln Asn Glu Ile Thr Leu Thr
1625                1630                1635

His Pro Val Thr Lys Tyr Ile Met Thr Cys Met Ser Ala Asp Leu
1640                1645                1650

Glu Val Val Thr Ser Thr Trp Val Leu Val Gly Gly Val Leu Ala
1655                1660                1665

Ala Leu Ala Ala Tyr Cys Leu Ser Thr Gly Cys Val Val Ile Val
1670                1675                1680

Gly Arg Val Val Leu Ser Gly Lys Pro Ala Ile Ile Pro Asp Arg
1685                1690                1695

Glu Val Leu Tyr Arg Glu Phe Asp Glu Met Glu Glu Cys Ser Gln
1700                1705                1710

His Leu Pro Tyr Ile Glu Gln Gly Met Met Leu Ala Glu Gln Phe
1715                1720                1725

Lys Gln Lys Ala Leu Gly Leu Leu Gln Thr Ala Ser Arg Gln Ala
1730                1735                1740

Glu Val Ile Ala Pro Ala Val Gln Thr Asn Trp Gln Lys Leu Glu
1745                1750                1755

Thr Phe Trp Ala Lys His Met Trp Asn Phe Ile Ser Gly Ile Gln
1760                1765                1770

Tyr Leu Ala Gly Leu Ser Thr Leu Pro Gly Asn Pro Ala Ile Ala
1775                1780                1785

Ser Leu Met Ala Phe Thr Ala Ala Val Thr Ser Pro Leu Thr Thr
1790                1795                1800

Ser Gln Thr Leu Leu Phe Asn Ile Leu Gly Gly Trp Val Ala Ala
1805                1810                1815

Gln Leu Ala Ala Pro Gly Ala Ala Thr Ala Phe Val Gly Ala Gly
1820                1825                1830

Leu Ala Gly Ala Ala Ile Gly Ser Val Gly Leu Gly Lys Val Leu
1835                1840                1845

Ile Asp Ile Leu Ala Gly Tyr Gly Ala Gly Val Ala
1850                1855                1860

<210> SEQ ID NO 2
<211> LENGTH: 646

<212> TYPE: PRT
<213> ORGANISM: Hepatitis C virus

<400> SEQUENCE: 2

```
Met Gly Cys Val Val Ile Val Gly Arg Val Val Leu Ser Gly Ser Gly
1               5                   10                  15

Ser Ile Thr Ala Tyr Ala Gln Gln Thr Arg Gly Leu Leu Gly Cys Lys
            20                  25                  30

Lys Thr Ser Leu Thr Gly Arg Asp Lys Asn Gln Val Glu Gly Glu Val
        35                  40                  45

Gln Ile Val Ser Thr Ala Ala Gln Thr Phe Leu Ala Thr Cys Ile Asn
    50                  55                  60

Gly Val Cys Trp Thr Val Tyr His Gly Ala Gly Thr Arg Thr Ile Ala
65                  70                  75                  80

Ser Pro Lys Gly Pro Val Ile Gln Met Tyr Thr Asn Val Asp Gln Asp
                85                  90                  95

Leu Val Gly Trp Pro Ala Pro Gln Gly Ser Arg Ser Leu Thr Pro Cys
            100                 105                 110

Thr Cys Gly Ser Ser Asp Leu Tyr Leu Val Thr Arg His Ala Asp Val
        115                 120                 125

Ile Pro Val Arg Arg Arg Gly Asp Ser Arg Gly Ser Leu Leu Ser Pro
    130                 135                 140

Arg Pro Ile Ser Tyr Leu Lys Gly Ser Ala Gly Gly Pro Leu Leu Cys
145                 150                 155                 160

Pro Ala Gly His Ala Val Gly Ile Phe Arg Ala Ala Val Cys Thr Arg
                165                 170                 175

Gly Val Ala Lys Ala Val Asp Phe Ile Pro Val Glu Asn Leu Glu Thr
            180                 185                 190

Thr Met Arg Ser Pro Val Phe Thr Asp Asn Ser Ser Pro Pro Val Val
        195                 200                 205

Pro Gln Ser Phe Gln Val Ala His Leu His Ala Pro Thr Gly Ser Gly
    210                 215                 220

Lys Ser Thr Lys Val Pro Ala Ala Tyr Ala Ala Gln Gly Tyr Lys Val
225                 230                 235                 240

Leu Val Leu Asn Pro Ser Val Ala Ala Thr Leu Gly Phe Gly Ala Tyr
                245                 250                 255

Met Ser Lys Ala His Gly Ile Asp Pro Asn Ile Arg Thr Gly Val Arg
            260                 265                 270

Thr Ile Thr Thr Gly Ser Pro Ile Thr Tyr Ser Thr Tyr Gly Lys Phe
        275                 280                 285

Leu Ala Asp Gly Gly Cys Ser Gly Gly Ala Tyr Asp Ile Ile Ile Cys
    290                 295                 300

Asp Glu Cys His Ser Thr Asp Ala Thr Ser Ile Leu Gly Ile Gly Thr
305                 310                 315                 320

Val Leu Asp Gln Ala Glu Thr Ala Gly Ala Arg Leu Val Val Leu Ala
                325                 330                 335

Thr Ala Thr Pro Pro Gly Ser Val Thr Val Pro His Pro Asn Ile Glu
            340                 345                 350

Glu Val Ala Leu Ser Thr Thr Gly Glu Ile Pro Phe Tyr Gly Lys Ala
        355                 360                 365

Ile Pro Leu Glu Val Ile Lys Gly Gly Arg His Leu Ile Phe Cys His
    370                 375                 380

Ser Lys Lys Lys Cys Asp Glu Leu Ala Ala Lys Leu Val Ala Leu Gly
385                 390                 395                 400
```

```
Ile Asn Ala Val Ala Tyr Tyr Arg Gly Leu Asp Val Ser Val Ile Pro
                405                 410                 415

Thr Ser Gly Asp Val Val Val Ala Thr Asp Ala Leu Met Thr Gly
            420                 425                 430

Tyr Thr Gly Asp Phe Asp Ser Val Ile Asp Cys Asn Thr Cys Val Thr
            435                 440                 445

Gln Thr Val Asp Phe Ser Leu Asp Pro Thr Phe Thr Ile Glu Thr Ile
    450                 455                 460

Thr Leu Pro Gln Asp Ala Val Ser Arg Thr Gln Arg Arg Gly Arg Thr
465                 470                 475                 480

Gly Arg Gly Lys Pro Gly Ile Tyr Arg Phe Val Ala Pro Gly Glu Arg
                485                 490                 495

Pro Ser Gly Met Phe Asp Ser Ser Val Leu Cys Glu Cys Tyr Asp Ala
            500                 505                 510

Gly Cys Ala Trp Tyr Glu Leu Thr Pro Ala Glu Thr Thr Val Arg Leu
        515                 520                 525

Arg Ala Tyr Met Asn Thr Pro Gly Leu Pro Val Cys Gln Asp His Leu
530                 535                 540

Glu Phe Trp Glu Gly Val Phe Thr Gly Leu Thr His Ile Asp Ala His
545                 550                 555                 560

Phe Leu Ser Gln Thr Lys Gln Ser Gly Glu Asn Leu Pro Tyr Leu Val
                565                 570                 575

Ala Tyr Gln Ala Thr Val Cys Ala Arg Ala Gln Ala Pro Pro Pro Ser
            580                 585                 590

Trp Asp Gln Met Trp Lys Cys Leu Ile Arg Leu Lys Pro Thr Leu His
            595                 600                 605

Gly Pro Thr Pro Leu Leu Tyr Arg Leu Gly Ala Val Gln Asn Glu Ile
    610                 615                 620

Thr Leu Thr His Pro Val Thr Lys Tyr Ile Met Thr Cys Met Ser Ala
625                 630                 635                 640

Asp Leu Glu Val Val Thr
                645

<210> SEQ ID NO 3
<211> LENGTH: 13
<212> TYPE: PRT
<213> ORGANISM: Hepatitis C virus

<400> SEQUENCE: 3

Gly Cys Val Val Ile Val Gly Arg Val Val Leu Ser Gly
1               5                   10

<210> SEQ ID NO 4
<211> LENGTH: 629
<212> TYPE: PRT
<213> ORGANISM: Hepatitis C virus

<400> SEQUENCE: 4

Ile Thr Ala Tyr Ala Gln Gln Thr Arg Gly Leu Leu Gly Cys Lys Lys
1               5                   10                  15

Thr Ser Leu Thr Gly Arg Asp Lys Asn Gln Val Glu Gly Glu Val Gln
            20                  25                  30

Ile Val Ser Thr Ala Ala Gln Thr Phe Leu Ala Thr Cys Ile Asn Gly
        35                  40                  45

Val Cys Trp Thr Val Tyr His Gly Ala Gly Thr Arg Thr Ile Ala Ser
    50                  55                  60
```

```
Pro Lys Gly Pro Val Ile Gln Met Tyr Thr Asn Val Asp Gln Asp Leu
 65                  70                  75                  80

Val Gly Trp Pro Ala Pro Gln Gly Ser Arg Ser Leu Thr Pro Cys Thr
                 85                  90                  95

Cys Gly Ser Ser Asp Leu Tyr Leu Val Thr Arg His Ala Asp Val Ile
            100                 105                 110

Pro Val Arg Arg Arg Gly Asp Ser Arg Gly Ser Leu Leu Ser Pro Arg
        115                 120                 125

Pro Ile Ser Tyr Leu Lys Gly Ser Ser Gly Gly Pro Leu Leu Cys Pro
    130                 135                 140

Ala Gly His Ala Val Gly Ile Phe Arg Ala Ala Val Cys Thr Arg Gly
145                 150                 155                 160

Val Ala Lys Ala Val Asp Phe Ile Pro Val Glu Asn Leu Glu Thr Thr
                165                 170                 175

Met Arg Ser Pro Val Phe Thr Asp Asn Ser Ser Pro Pro Val Val Pro
            180                 185                 190

Gln Ser Phe Gln Val Ala His Leu His Ala Pro Thr Gly Ser Gly Lys
        195                 200                 205

Ser Thr Lys Val Pro Ala Ala Tyr Ala Ala Gln Gly Tyr Lys Val Leu
    210                 215                 220

Val Leu Asn Pro Ser Val Ala Ala Thr Leu Gly Phe Gly Ala Tyr Met
225                 230                 235                 240

Ser Lys Ala His Gly Ile Asp Pro Asn Ile Arg Thr Gly Val Arg Thr
                245                 250                 255

Ile Thr Thr Gly Ser Pro Ile Thr Tyr Ser Thr Tyr Gly Lys Phe Leu
            260                 265                 270

Ala Asp Gly Gly Cys Ser Gly Gly Ala Tyr Asp Ile Ile Ile Cys Asp
        275                 280                 285

Glu Cys His Ser Thr Asp Ala Thr Ser Ile Leu Gly Ile Gly Thr Val
    290                 295                 300

Leu Asp Gln Ala Glu Thr Ala Gly Ala Arg Leu Val Val Leu Ala Thr
305                 310                 315                 320

Ala Thr Pro Pro Gly Ser Val Thr Val Pro His Pro Asn Ile Glu Glu
                325                 330                 335

Val Ala Leu Ser Thr Thr Gly Glu Ile Pro Phe Tyr Gly Lys Ala Ile
            340                 345                 350

Pro Leu Glu Val Ile Lys Gly Gly Arg His Leu Ile Phe Cys His Ser
        355                 360                 365

Lys Lys Lys Cys Asp Glu Leu Ala Ala Lys Leu Val Ala Leu Gly Ile
    370                 375                 380

Asn Ala Val Ala Tyr Tyr Arg Gly Leu Asp Val Ser Val Ile Pro Thr
385                 390                 395                 400

Ser Gly Asp Val Val Val Ala Thr Asp Ala Leu Met Thr Gly Tyr
                405                 410                 415

Thr Gly Asp Phe Asp Ser Val Ile Asp Cys Asn Thr Cys Val Thr Gln
            420                 425                 430

Thr Val Asp Phe Ser Leu Asp Pro Thr Phe Thr Ile Glu Thr Ile Thr
        435                 440                 445

Leu Pro Gln Asp Ala Val Ser Arg Thr Gln Arg Arg Gly Arg Thr Gly
    450                 455                 460

Arg Gly Lys Pro Gly Ile Tyr Arg Phe Val Ala Pro Gly Glu Arg Pro
465                 470                 475                 480
```

```
Ser Gly Met Phe Asp Ser Ser Val Leu Cys Glu Cys Tyr Asp Ala Gly
                485                 490                 495

Cys Ala Trp Tyr Glu Leu Thr Pro Ala Glu Thr Thr Val Arg Leu Arg
            500                 505                 510

Ala Tyr Met Asn Thr Pro Gly Leu Pro Val Cys Gln Asp His Leu Glu
        515                 520                 525

Phe Trp Glu Gly Val Phe Thr Gly Leu Thr His Ile Asp Ala His Phe
    530                 535                 540

Leu Ser Gln Thr Lys Gln Ser Gly Glu Asn Leu Pro Tyr Leu Val Ala
545                 550                 555                 560

Tyr Gln Ala Thr Val Cys Ala Arg Ala Gln Ala Pro Pro Ser Trp
                565                 570                 575

Asp Gln Met Trp Lys Cys Leu Ile Arg Leu Lys Pro Thr Leu His Gly
                580                 585                 590

Pro Thr Pro Leu Leu Tyr Arg Leu Gly Ala Val Gln Asn Glu Ile Thr
            595                 600                 605

Leu Thr His Pro Val Thr Lys Tyr Ile Met Thr Cys Met Ser Ala Asp
        610                 615                 620

Leu Glu Val Val Thr
625

<210> SEQ ID NO 5
<211> LENGTH: 10
<212> TYPE: DNA
<213> ORGANISM: Artificial Sequence
<220> FEATURE:
<223> OTHER INFORMATION: Primer

<400> SEQUENCE: 5
acaaaacaaa                                                          10

<210> SEQ ID NO 6
<211> LENGTH: 26
<212> TYPE: DNA
<213> ORGANISM: Artificial Sequence
<220> FEATURE:
<223> OTHER INFORMATION: Primer

<400> SEQUENCE: 6
ctagggtgca agaagaccag cctaac                                        26

<210> SEQ ID NO 7
<211> LENGTH: 19
<212> TYPE: DNA
<213> ORGANISM: Artificial Sequence
<220> FEATURE:
<223> OTHER INFORMATION: Primer

<400> SEQUENCE: 7
aggctggtct tcttgcacc                                                19

<210> SEQ ID NO 8
<211> LENGTH: 33
<212> TYPE: DNA
<213> ORGANISM: Artificial Sequence
<220> FEATURE:
<223> OTHER INFORMATION: Primer

<400> SEQUENCE: 8
tgtcggccga cctggaggtc gtcacgtgat aag                                33
```

-continued

```
<210> SEQ ID NO 9
<211> LENGTH: 41
<212> TYPE: DNA
<213> ORGANISM: Artificial Sequence
<220> FEATURE:
<223> OTHER INFORMATION: Primer

<400> SEQUENCE: 9
tcgacttatc acgtgacgac ctccaggtcg gccgacatgc a                    41
```